United States Patent
Logan et al.

(10) Patent No.: US 8,621,213 B2
(45) Date of Patent: Dec. 31, 2013

(54) REMOTE CONTROL OF MEDICAL DEVICES USING INSTANT MESSAGING INFRASTRUCTURE

(75) Inventors: Mark Logan, Pickering (CA); John Fehrenbach, Mequon, WI (US)

(73) Assignee: Merge Healthcare, Inc., Hartland, WI (US)

(*) Notice: Subject to any disclaimer, the term of this patent is extended or adjusted under 35 U.S.C. 154(b) by 325 days.

(21) Appl. No.: 12/911,468

(22) Filed: Oct. 25, 2010

(65) Prior Publication Data
US 2011/0302414 A1 Dec. 8, 2011

Related U.S. Application Data

(60) Provisional application No. 61/352,704, filed on Jun. 8, 2010, provisional application No. 61/352,700, filed on Jun. 8, 2010.

(51) Int. Cl.
*H04L 29/06* (2006.01)

(52) U.S. Cl.
USPC ........... 713/168; 713/155; 380/277; 380/284; 380/285; 709/206; 709/207; 370/352; 725/109

(58) Field of Classification Search
USPC ............... 707/101, 102, 104.1; 709/206, 207; 370/352; 725/109; 713/155; 380/277, 380/284, 285
See application file for complete search history.

(56) References Cited

U.S. PATENT DOCUMENTS

| | | | |
|---|---|---|---|
| 6,353,848 B1 | 3/2002 | Morris | |
| 6,381,029 B1 | 4/2002 | Tipirneni | |
| 6,430,604 B1 | 8/2002 | Ogle et al. | |
| 6,442,432 B2 | 8/2002 | Lee | |
| 6,501,834 B1 | 12/2002 | Milewski et al. | |
| 6,549,937 B1 | 4/2003 | Auerbach et al. | |
| 6,572,585 B2 | 6/2003 | Choi | |
| 6,691,162 B1 | 2/2004 | Wick | |
| 6,714,982 B1 | 3/2004 | McDonough et al. | |
| 6,732,364 B1 | 5/2004 | Bhaskaran et al. | |

(Continued)

FOREIGN PATENT DOCUMENTS

| WO | WO0233867 | 4/2002 |
|---|---|---|
| WO | WO2006086089 | 8/2006 |

OTHER PUBLICATIONS

P. Saint-Andre, Ed., Extensible Messaging and Presence Protocol (XMPP): Instant Messaging and Presence, Oct. 2004, pp. 1-107, The Internet Society.

(Continued)

*Primary Examiner* — Brandon Hoffman
*Assistant Examiner* — Hee Song
(74) *Attorney, Agent, or Firm* — Michael Best & Friedrich LLP

(57) ABSTRACT

Systems and methods for remote control and management of medical workstations using an instant messaging infrastructure. A remote client, such as a mobile phone, laptop, tablet, or other computing device, is used to generate instructions or information requests in one or more data packets. The remote client sends the one or more data packets using the instant messaging infrastructure to a medical workstation at another location. A service application in communication with the medical workstation receives the data packets and causes the medical workstation to retrieve the requested information or execute the instruction. The communications between the remote client and the service application are encrypted and signed to ensure secure communications.

31 Claims, 31 Drawing Sheets

(56) References Cited

U.S. PATENT DOCUMENTS

| | | | |
|---|---|---|---|
| 6,768,425 | B2 | 7/2004 | Flaherty et al. |
| 6,829,378 | B2 | 12/2004 | DiFilippo et al. |
| 6,839,735 | B2 | 1/2005 | Wong et al. |
| 6,907,447 | B1 | 6/2005 | Cooperman et al. |
| 6,907,571 | B2 | 6/2005 | Slotznick |
| 6,993,564 | B2 | 1/2006 | Whitten, II |
| 7,039,676 | B1 | 5/2006 | Day et al. |
| 7,051,119 | B2 | 5/2006 | Shafron et al. |
| 7,054,617 | B2 | 5/2006 | Thomsen et al. |
| 7,124,370 | B2 | 10/2006 | Fish |
| 7,142,646 | B2 | 11/2006 | Zafar et al. |
| 7,184,785 | B2 | 2/2007 | Balley et al. |
| 7,188,151 | B2 | 3/2007 | Kumar et al. |
| 7,216,167 | B2 | 5/2007 | Hamilton, II et al. |
| 7,219,303 | B2 | 5/2007 | Fish |
| 7,221,945 | B2 | 5/2007 | Milford et al. |
| 7,229,006 | B2 | 6/2007 | Babbi et al. |
| 7,231,443 | B2 | 6/2007 | Hamilton, II et al. |
| 7,269,627 | B2 | 9/2007 | Knauerhase |
| 7,272,662 | B2 | 9/2007 | Chesnais et al. |
| 7,310,659 | B1 | 12/2007 | George |
| 7,346,630 | B2 | 3/2008 | Eichstaedt et al. |
| 7,346,658 | B2 | 3/2008 | Simpson |
| 7,353,247 | B2 | 4/2008 | Hough et al. |
| 7,366,779 | B1 | 4/2008 | Crawford |
| 7,437,481 | B2 | 10/2008 | Bond et al. |
| 7,444,588 | B2 | 10/2008 | Hill et al. |
| 7,461,378 | B2 | 12/2008 | Beyda |
| 7,475,240 | B2 | 1/2009 | Shah et al. |
| 7,487,220 | B1 | 2/2009 | Mahawadiwar |
| 7,490,076 | B2 | 2/2009 | Mu et al. |
| 7,506,029 | B2 | 3/2009 | Sanjeeva et al. |
| 7,509,377 | B2 | 3/2009 | Harvey et al. |
| 7,512,619 | B2 | 3/2009 | Burkhardt |
| 7,519,661 | B2 | 4/2009 | Slotznick |
| 7,519,912 | B2 | 4/2009 | Moody et al. |
| 7,529,796 | B2 | 5/2009 | Riddle |
| 7,539,727 | B2 | 5/2009 | Miller et al. |
| 7,539,732 | B2 | 5/2009 | Kelso et al. |
| 7,552,183 | B2 | 6/2009 | Coletrane et al. |
| 7,554,938 | B1 | 6/2009 | Smith et al. |
| 7,558,828 | B1 | 7/2009 | Panzer |
| 7,561,595 | B2 | 7/2009 | Garcia-Martin et al. |
| 7,562,116 | B2 | 7/2009 | Barsness |
| 7,568,007 | B2 | 7/2009 | Narayanaswami et al. |
| 7,571,190 | B2 | 8/2009 | Nguyen et al. |
| 7,809,816 | B2* | 10/2010 | Johnson et al. ............... 709/223 |
| 2002/0036990 | A1 | 3/2002 | Chodor et al. |
| 2002/0090068 | A1 | 7/2002 | Song |
| 2003/0163580 | A1 | 8/2003 | Lee |
| 2004/0177116 | A1 | 9/2004 | McConn et al. |
| 2004/0260790 | A1 | 12/2004 | Balloni et al. |
| 2005/0021624 | A1 | 1/2005 | Herf et al. |
| 2006/0122482 | A1 | 6/2006 | Mariotti et al. |
| 2007/0197878 | A1 | 8/2007 | Shklarski |
| 2007/0208808 | A1 | 9/2007 | Rust |
| 2007/0232942 | A1 | 10/2007 | Quy |
| 2008/0068200 | A1* | 3/2008 | Bootes .................... 340/815.45 |
| 2008/0071895 | A1 | 3/2008 | Johnson et al. |
| 2008/0081979 | A1 | 4/2008 | Solliday-McRoy |
| 2008/0148328 | A1* | 6/2008 | Runne .......................... 725/109 |
| 2008/0177154 | A1 | 7/2008 | Hansen et al. |
| 2008/0177155 | A1 | 7/2008 | Hansen et al. |
| 2008/0312584 | A1 | 12/2008 | Montgomery et al. |
| 2008/0312585 | A1 | 12/2008 | Brukalo et al. |
| 2009/0121865 | A1 | 5/2009 | Hamel et al. |
| 2009/0150517 | A1 | 6/2009 | Atsmon et al. |
| 2009/0203973 | A1 | 8/2009 | Donoghue et al. |
| 2009/0237490 | A1 | 9/2009 | Nelson, Jr. |
| 2009/0254627 | A1* | 10/2009 | Morris ......................... 709/206 |
| 2009/0271873 | A1 | 10/2009 | Ram et al. |
| 2009/0282371 | A1 | 11/2009 | Curl |
| 2009/0300125 | A1 | 12/2009 | Wang et al. |
| 2009/0306573 | A1 | 12/2009 | Gagner et al. |
| 2009/0313377 | A1 | 12/2009 | Crawford |
| 2010/0004010 | A1 | 1/2010 | Shin et al. |
| 2010/0005156 | A1 | 1/2010 | Wesby |
| 2010/0153491 | A1 | 6/2010 | Li |
| 2010/0160759 | A1 | 6/2010 | Celentano et al. |
| 2010/0160860 | A1 | 6/2010 | Celentano et al. |

OTHER PUBLICATIONS

Public-key cryptography, Wikipedia pages, 2 pages, Retrieved Oct. 7, 2010, from http://en.wikipedia.org/wiki/Public_key.

Certificate Authority, Wikipedia pages, 4 pages, Retrieved Oct. 4, 2010, from http://en.wikipedia.org/wiki/Certificate_authority.

Internet Socket, Wikipedia pages, 4 pages, Retrieved Oct. 4, 2010, from http://en.wikipedia.org/wiki/Internet_socket.

Extensible Messaging and Presence Protocol, Wikipedia pages, 7 pages, Retrieved Oct. 4, 2010, from http://en.wikipedia.org/wiki/Xmpp.

Proxy Server, Wikipedia pages, 9 pages, Retrieved Oct. 4, 2010, from http://en.wikipedia.org/wiki/Proxy_server.

MIM Software—Mobile MIM for the iPhone & iPad, webpages, 3 pages, Retrieved Oct. 25, 2010, from http://www.mimsoftware.com/products/iphone.

ResolutionMD Mobile, Calgary Scientific webpages, 2 pages, Retrieved Oct. 25, 2010, from http://www.calgaryscientific.com/index.php?id=5.

Osirix—Viewer iPhone Application, User Manual, updated, pp. 1-15, retrieved on Oct. 25, 2010 from www.osirix-viewer.com.

Calgary Scientific, Inc., ResolutionMD Mobile Feature List, updated, 1 page, Calgary, AB, retrieved on Oct. 25, 2010 from www.calgaryscientific.com.

* cited by examiner

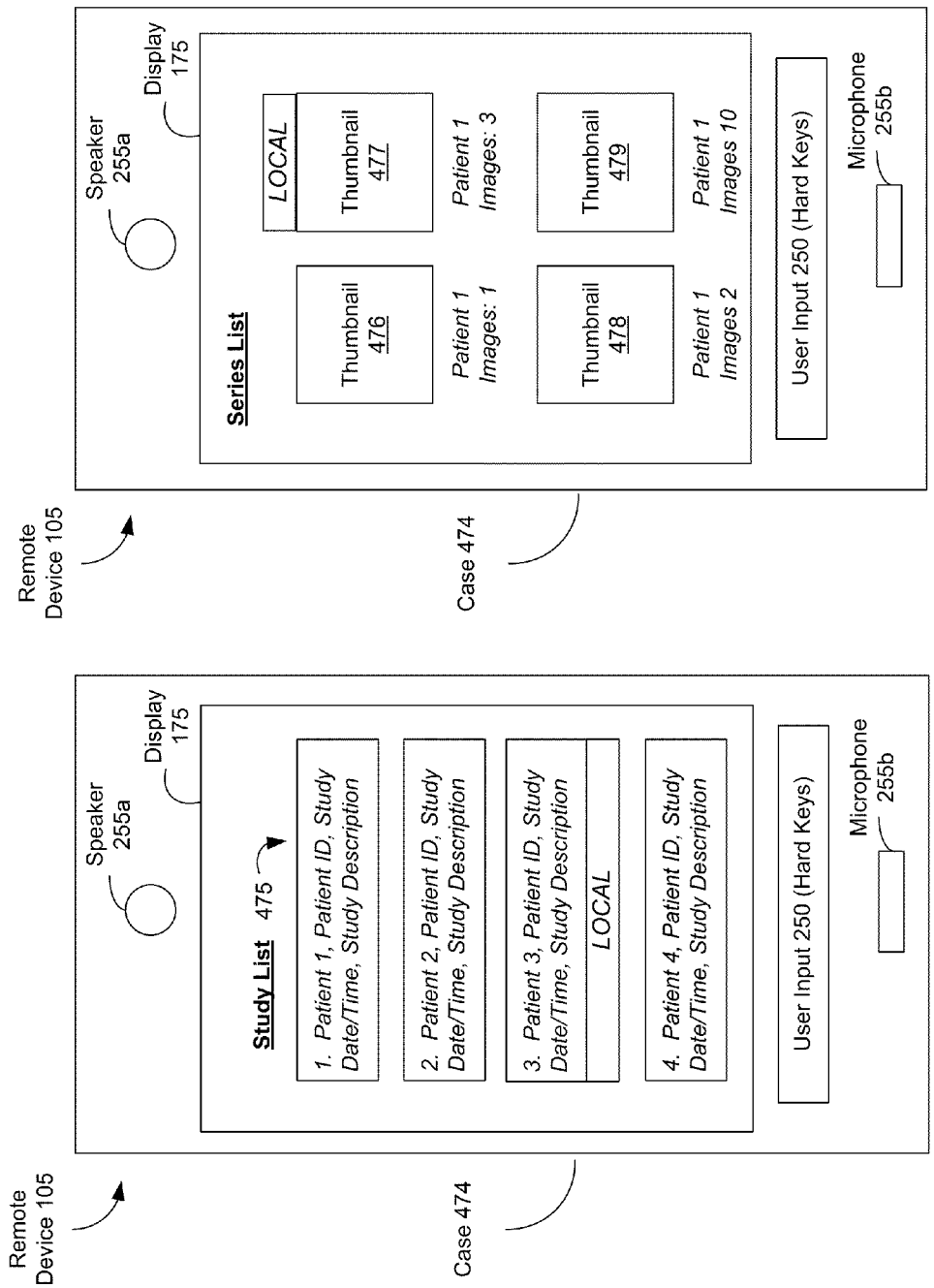

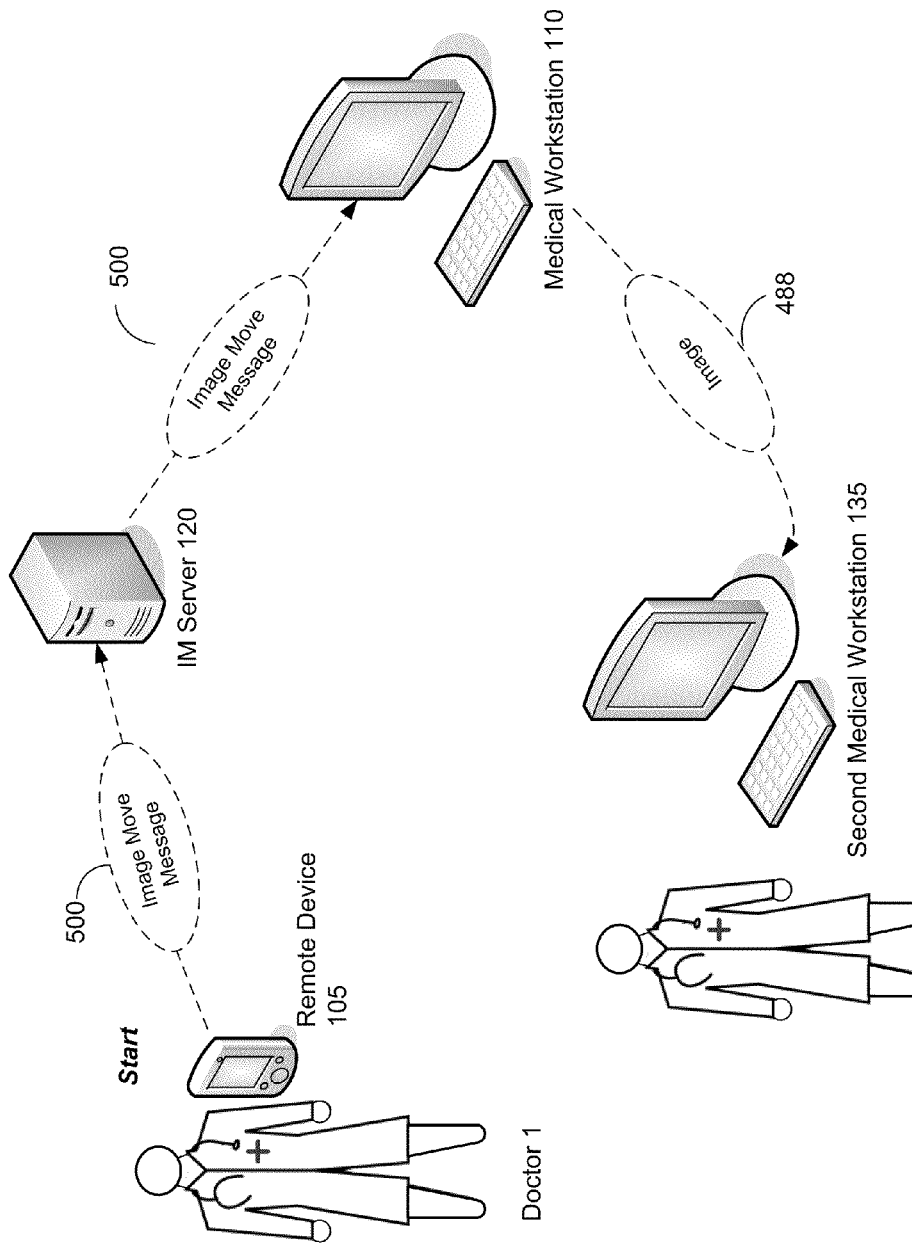

REMOTE CONTROL OF MEDICAL DEVICES USING INSTANT MESSAGING INFRASTRUCTURE

RELATED APPLICATIONS

The present application claims priority to U.S. Provisional Patent Application Ser. No. 61/352,704, filed Jun. 8, 2010, and U.S. Provisional Patent Application Ser. No. 61/352,700, filed Jun. 8, 2010, the entire contents of each of which are hereby incorporated by reference.

FIELD OF THE INVENTION

The present invention relates to remote control of medical devices.

SUMMARY

In some embodiments, the invention provides a system for remote control and management of medical workstations. The system includes a remote client, a web server, an instant messaging (IM) server, a medical workstation, and a remote instant message client (BOT) that communicate using an instant messaging infrastructure. The remote client includes a client IM application and the medical workstation includes a service application, each being used to form a connection therebetween and to transfer data packets over the IM infrastructure.

In some embodiments, the invention provides a method of transferring medical images from a remote medical image database to a destination device using an instant messaging (IM) infrastructure. The method includes establishing a session between a local device and an IM server; sending a presence message to a remote medical workstation via the IM server, wherein the remote medical workstation communicates with a medical image database; and receiving, by the local device, presence information for the remote medical workstation from the IM server. The method further includes the local device sending an image availability query message to the remote medical workstation via the IM server and obtaining image availability data from the remote medical workstation via the IM server. The image availability data indicates an image that is available on the remote medical image database. The local device further displays a representation of the image available on the remote medical image database and receives a user selection of the image. The method also includes sending an image command message, based on the user selection, to the remote medical workstation via the IM server. The image command message instructs the remote medical workstation to transmit a copy of the image to the destination device. The destination device may be the local device or another medical workstation.

In some embodiments, the invention provides a method of transmitting medical images from a medical image database to a remote device using an instant messaging (IM) infrastructure. The method includes establishing a first session between an IM server and the remote device, and a second session between the IM server and a medical image workstation. The medical image workstation is in communication with a medical image database, for instance, to obtain medical images for display on the medical image workstation and to provide them to other devices. The method further includes the IM server sending roster and presence information to the remote device based on a roster request message received from the remote device; forwarding an image availability query message from the remote device to the medical image workstation; and forwarding image availability data received from the medical image workstation to the remote device. The image availability data includes a representation of an image available on the medical image database. The IM server also forwards an image command message with an image selection received from the remote device to the medical image workstation. The image command message instructs the medical image workstation to transfer a copy of the selected image to a destination device.

In some embodiments, the invention provides a method of transmitting medical images from a medical image database to a remote device using an instant messaging (IM) infrastructure. The method includes establishing a session with an IM server. The method also includes the medical workstation receiving presence information for the remote device from the IM server and receiving an image availability query message from the remote device via the IM server. The medical workstation is in communication with the medical image database, for instance, to obtain medical images for display on the medical workstation and to provide them to other devices. The medical workstation transmits image availability data to the remote device via the IM server. The image availability data includes a representation of an image available on the medical image database. The method further includes receiving an image command message with an image selection from the remote device via the IM server. The image selection selects the image available on the medical image database for transmission. The medical image database then transmits a copy of the image to a destination device in response to the image command message.

In some embodiments, the invention provides an instant messaging (IM) server enabling instant message communication between a medical image workstation and a requesting device. The medical image workstation is in communication with a medical image database, for instance, to obtain medical images for display on the medical image workstation and to provide them to other devices. The IM server includes a memory, a session establishing module, and a message routing module. The memory includes a requesting device roster including an identification for the medical image workstation; a medical image workstation roster including an identification for the requesting device; and presence information indicating presence status of the requesting device and the medical image workstation. The session establishing module establishes a first instant message session between the IM server and the requesting device, and establishes a second instant message session between the IM server and the medical image workstation. The message routing module forwards an image availability query message from the requesting device to the medical image workstation, forwards image availability data received from the medical image workstation to the requesting device, and forwards an image command message with an image selection from the requesting device to the medical image workstation. The image availability data includes a representation of an image available on the medical image database. The image command message instructs the medical image workstation to transfer a copy of the selected image to a destination device.

In some embodiments, the invention provides a method of establishing a secure instant message (IM) session between a local device and a remote medical workstation. The method includes creating an IM account for the local device on an IM server by submitting registration information to a registration server. The registration server communicates with the IM server to create an IM account identifier using the registration information, to add the IM account identifier to a first roster associated with a registration BOT maintained by the IM server, and to add a BOT identifier to a second roster associated with the IM account identifier. The method also includes the local device receiving a temporary unique ID from the remote medical workstation. The registration BOT provides the temporary unique ID to the remote medical. The local device also requests that the registration BOT add the remote medical workstation to the second roster and add the local device to a third roster associated with the remote medical workstation. The request, however, is denied unless the temporary unique ID is provided to the registration BOT. The method further includes the local device sending a message via the IM server to the remote medical workstation. The message requests transmission of an image on the remote medical workstation to a destination device.

In some embodiments, the invention provides a client instant messaging (IM) application stored on a computer readable medium. When executed by the processor of a local device, the client IM application performs multiple steps. The client IM application establishes a session between the local device and an IM server and sends a presence message to a remote medical workstation via the IM server. The remote medical workstation communicates with a medical image database, for instance, to obtain medical images for display on the remote medical workstation and to provide them to other devices. The client IM application also receives presence information for the remote medical workstation from the IM server and sends an image availability query message to the remote medical workstation via the IM server. The client IM application obtains image availability data from the remote medical workstation via the IM server. The image availability data indicates an image that is available on a remote medical image database. The client IM application then displays, on a display screen of the local device, a representation of the image available on the remote medical image database. The user selects an image and the selection is received by the client IM application. The client IM application then sends an image command message, based on the user selection, to the remote medical workstation via the IM server. The image command message instructs the remote medical workstation to transmit a copy of the image to a destination device. The computer readable medium includes, for instance, a computer hard drive, compact disc, floppy disc, flash drive, or other memory device.

In some embodiments, the invention provides a medical workstation that is remotely controllable by a remote device via an instant messaging (IM) server. The medical workstation includes a processor and a service application, which, when executed by the processor, performs multiple steps. The service application establishes a session with the IM server and receives presence information for the remote device from the IM server. The service application also receives an image availability query message from the remote device via the IM server and transmits image availability data to the remote device via the IM server. The image availability data includes a representation of an image available on the medical image database. The service application further receives an image command message with an image selection from the remote device via the IM server. The image selection selects the image available on the medical image database for transmission. In response to the image command message, the service application transmits a copy of the image to a destination device.

Other aspects of the invention will become apparent by consideration of the detailed description and accompanying drawings.

BRIEF DESCRIPTION OF THE DRAWINGS

FIGS. 14A-B depict a remote device.
FIGS. 17A-B illustrate a message flow for image move messages.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Embodiments of the invention allow for secure control and management of a medical workstation by a remote device over an instant messaging (IM) infrastructure. An IM infrastructure enables at least two client devices to communicate messages according to an IM protocol via an IM server. The IM infrastructure provides near real time delivery of queries, requests, and commands, which eliminates delays found in systems where requests are queued and polled for by the receiver. Among other functions, the IM server maintains a roster for each client device, maintains presence information indicating the availability of each client device, provides certain roster and presence information to appropriate client devices, and routes instant messages between two or more client devices. The IM protocol provides a set of rules governing the format of messages that are exchanged between the client devices and the IM server. The IM protocol also specifies when and how a client device or IM server should send a message or react to a received message.

In some embodiments, a mobile phone is operable to request via an IM infrastructure that an image accessible to the medical workstation be sent back to the mobile phone or to another workstation. The use of an IM infrastructure to control a remote medical workstation enables a simpler configuration and network management relative to, for instance, use of web browser-based connections or other network connections between devices. Additionally, embodiments of the system and method are secure as the network traffic is encrypted and the data packets including medical information are both encrypted and signed. The encrypted and signed data packet ensures that the data is being received from the correct sender and that only the intended recipient can decrypt the data.

Figure 1:
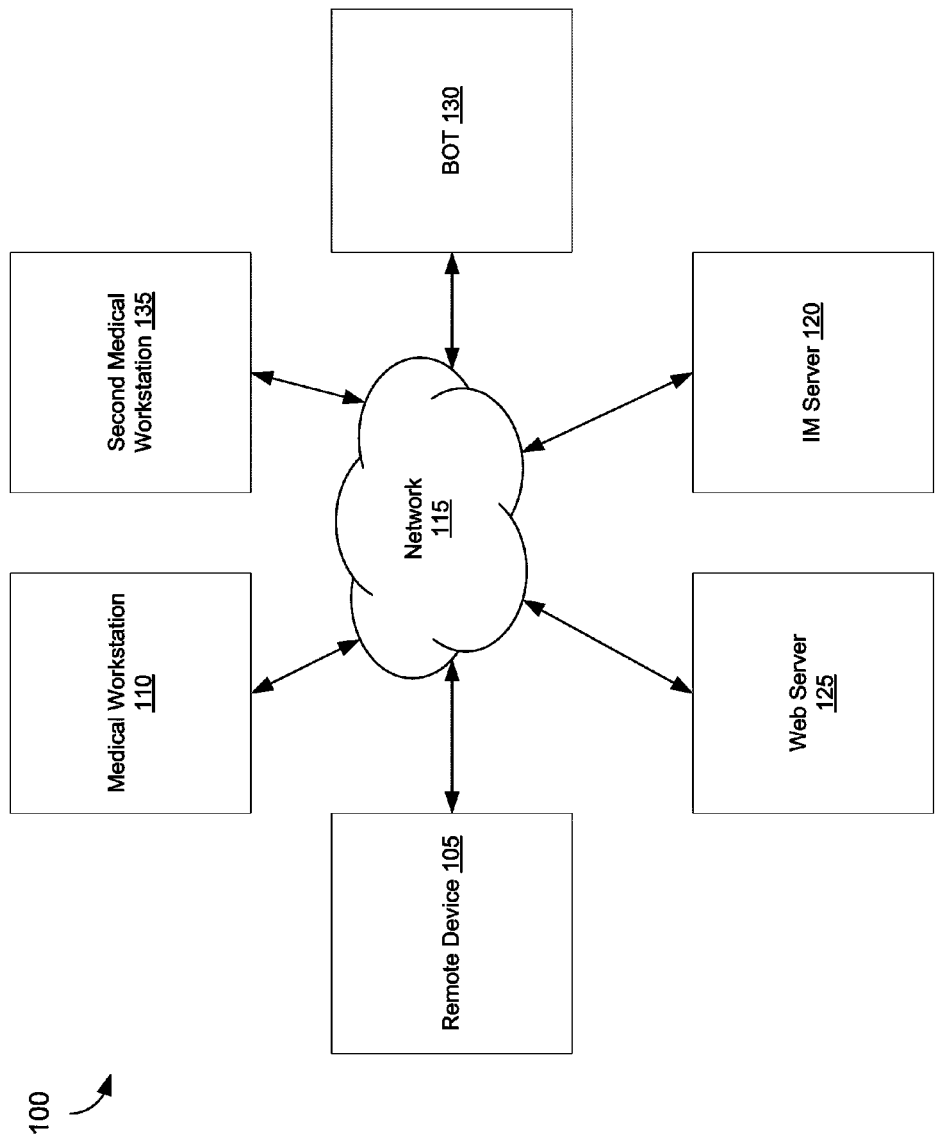
FIG. 1 depicts a system for remote control and management of medical workstations according to embodiments of the invention.

FIG. 1 depicts a system 100 in which a remote device 105 remotely controls and manages a medical workstation 110. The remote device 105 accesses and/or controls a medical workstation 110 operating in a remote location via a network 115. For instance, the medical workstation 110 is often located in a different room, building, campus, city, or country. The network 115 is one or more of the Internet, a local area network (LAN), a wide area network (WAN), and other computer networks. The devices that are coupled to the network 115, such as the remote device 105 and medical workstation 110, are directly coupled or indirectly coupled by way of, e.g., a hub, router, or similar device. Such couplings include wired connections (universal serial bus (USB), Ethernet, etc.), wireless connections (e.g., Bluetooth, WiFi, cellular, etc.) or a combination thereof.

The system 100 further includes an instant messaging (IM) server 120, a web server 125, and a remote instant message client (BOT) 130. The IM server 120 enables communications between the remote device 105 and the medical workstation 110. The web server 125 and BOT 130 are used to register a remote device 105 and a medical workstation 110 with the IM server 120 and to alter roster information for the remote device 105 and medical workstation 110. The system 100 is expandable to include multiple remote devices 105 and multiple medical workstations 110. For instance, system 100 includes a second medical workstation 135. Thus, in some embodiments, one or more remote clients 105 are operable to control one or more medical workstations 110 via the IM server 120.

Remote Device

Figure 2:
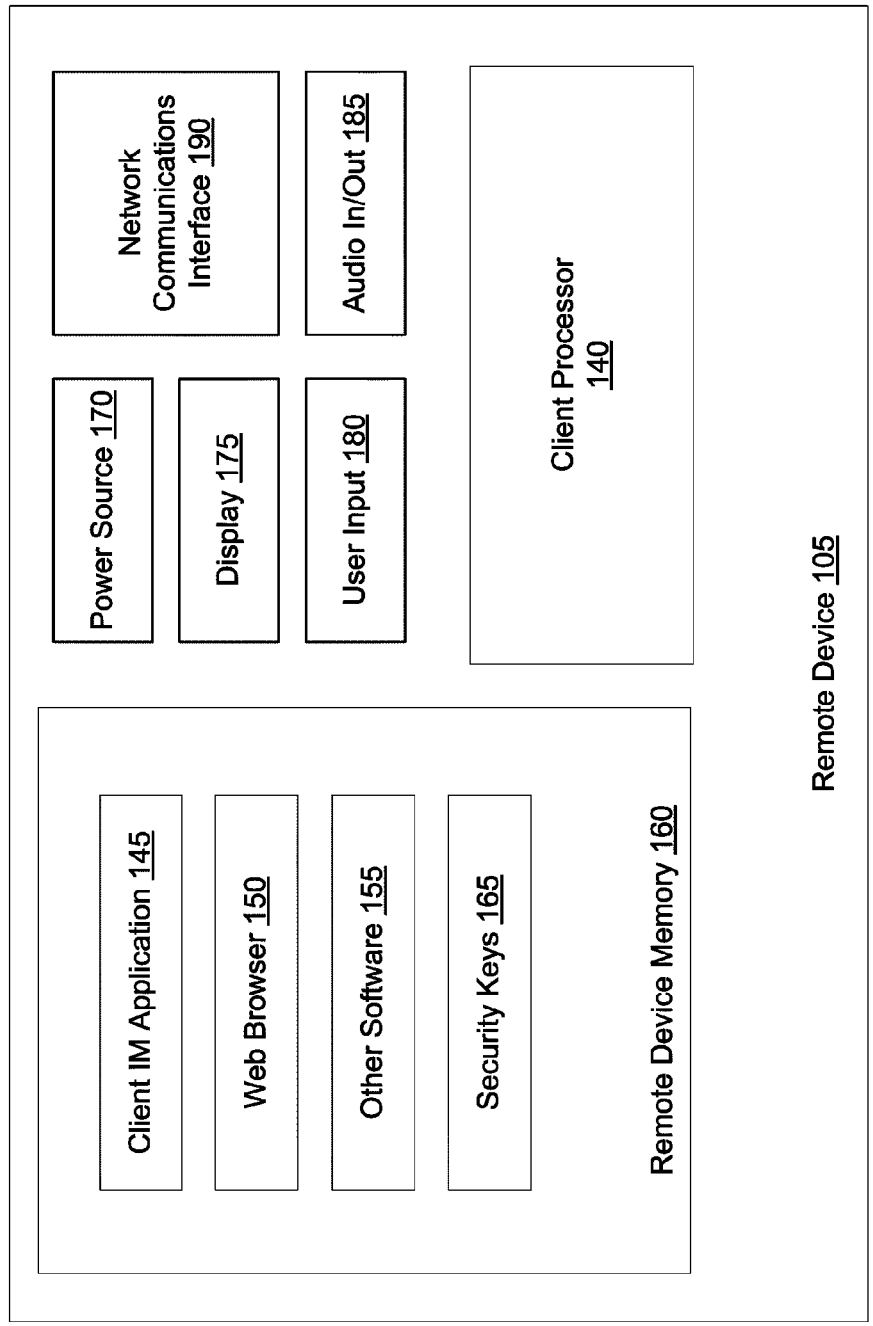
FIG. 2 depicts a remote device.

The remote device 105 is one of a personal computer, kiosk, tablet, laptop, mobile phone device (e.g., an iPhone™, Blackberry™, Droid™, etc.), or other computing device with an ability to connect to the network 115. As shown in FIG. 2, the remote device 105 includes a processor 140 that executes a client IM application 145, a web browser 150, and other software 155 stored in memory 160. In some embodiments, one or more of the software programs are stored remotely from the remote device 105 or are implemented partially or completely in hardware (e.g., using a field programmable gate array (FPGA) or application specific integrated circuit (ASIC)). The remote device 105 also stores security keys 165 within the memory 160, which are used for secure communications and will be explained in greater detail below. The remote device 105 further includes a power source 170, a display 175 (e.g., a touch screen display), user inputs 180 (e.g., push buttons, scroll wheels, etc.), audio in/out module 185 (e.g., including a microphone and speaker), and a network communications interface 190 for interfacing with the network 115. The power source 170 is, for instance, a battery that provides power to the components of the remote device 105. In some instances, the power source 170 receives power from an external battery, wall outlet, or other external power source, and provides the power to components of the remote device 105.

A user of remote device 105 uses the client IM application 145 to register with the IM server 120 and to send and receive queries, requests, and commands to other devices connected to the IM server 120 (e.g., the medical workstation 110). In some embodiments, the client IM application 145 is pre-loaded on the remote device 105. In other embodiments, the client IM application 145 is downloaded from an online repository (e.g., App Store™ for iPhone™ mobile phones, Android Market™ for Droid™ mobile phones) directly accessible by the remote device 105. In still other embodiments, the client IM application 145 is downloaded from an online repository to an independent computer using, for example, iTunes™ or Google Chrome™ and, thereafter, loaded from the independent computer to the remote device 105.

The client IM application 145 provides a graphical user interface (GUI) on the display 175 of the remote device 105. The GUI enables the user to interact with the client IM application 145 by way of the display 175, user input 180, and audio in/out 185.

Medical Workstation

Figure 3A:
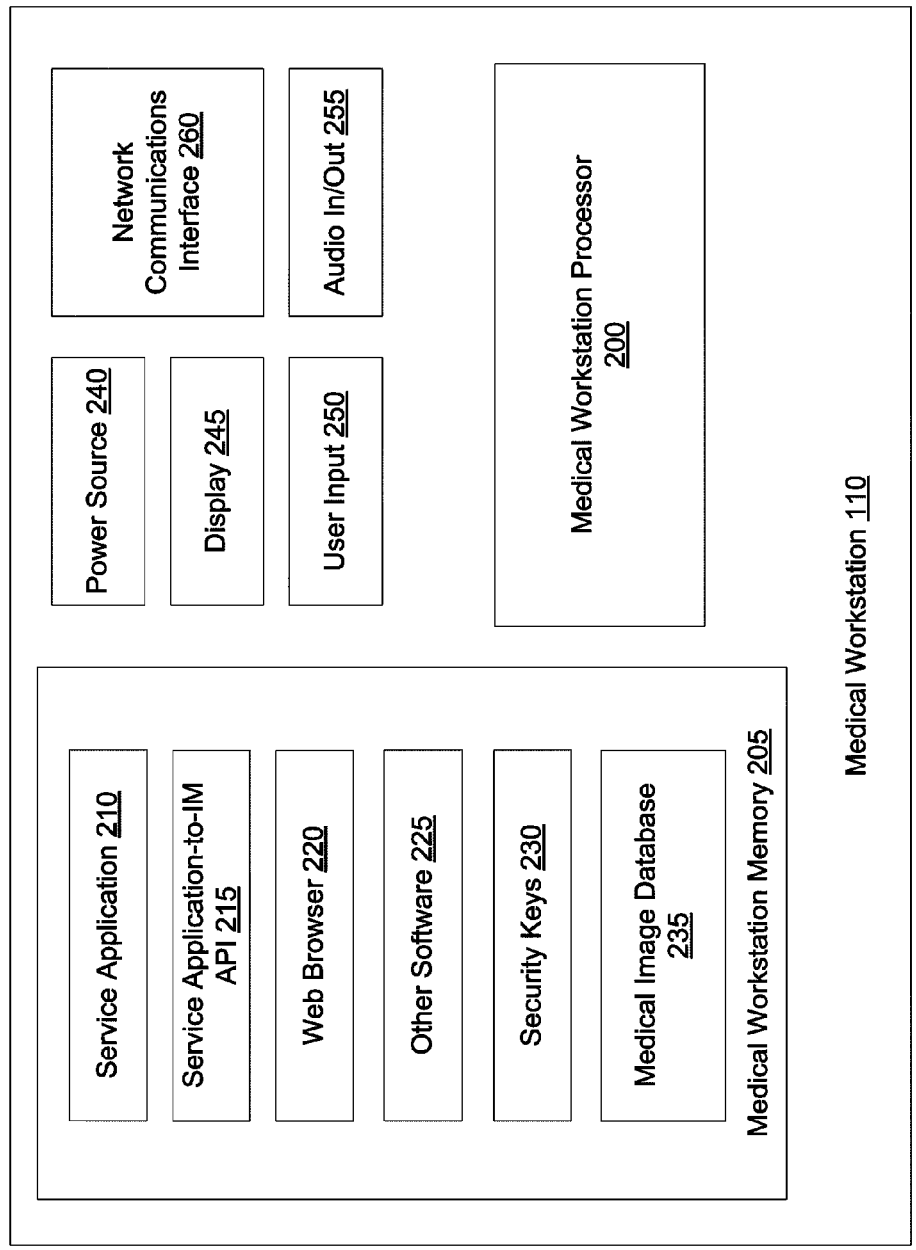
FIG. 3A depicts a medical workstation.

FIG. 3A depicts the medical workstation 110 according to some embodiments of the invention. The medical workstation 110 includes a processor 200 and a memory 205. The memory 205 includes a service application 210, a service application-to-IM application program interface (API) 215, a web browser 220, other software 225, security keys 230, and a medical image database 235. The service application 210, API 215, web browser 220, and other software are all executable by the processor 200. The medical workstation 110 includes a power source 240, display 245, user input 250, audio in/out 255, and network communications interface 260, which, in general, each function similarly to their counterparts in the remote device 105.

The medical workstation 110 is usable as a stand-alone device for viewing and/or manipulating medical images stored in the medical image database 235 on the display 245. For instance, the service application 210 and/or other software 225 is executed on the processor 200, which provides a GUI on the display 245 that a user interacts with to retrieve images within the medical image database 235. In some instances the user is a medical professional that evaluates images using the medical workstation 110 to diagnosis a patient depicted in the image. The user is also able to interact with the GUI to move images from the medical image database 235 to a database of another medical workstation or other destination. In some instances, the medical workstation 110 is a workstation in an electronic picture archiving and communication system (PACS).

The images within the medical image database 235 include computed tomography (CAT scan) images, magnetic resonance imaging (MRI) images, x-ray images, and other graphical depictions of patient medical information.

The service application 210, in combination with the API 215, is executed by the processor 200 and is used for interfacing with the IM server 120 to communicate with the remote device 105. Instant messages sent to the medical workstation 110 from the IM server 120 are received and translated by the API 215 in a protocol used by the service application 210. The instant messages are then forwarded to the service application 210. Vice versa, outgoing instructions and data from the service application 210 to the IM server 120 are translated by the API 215 into the IM protocol of the IM server 120.

Although the service application 210, API 215, web browser 220, other software 225, security keys 230, and medical image database 235 are all described as being stored on memory 205 locally, one or more of these items may be stored in an external memory in communication with the medical workstation 110. For instance, in some embodiments, the medical image database 235 is stored on an external USB hard drive or on a network hard drive. In some embodiments, one or more of the service application 210, API 215, web browser 220, other software 225, and security keys 230 are implemented partially or completely in hardware (e.g., using an FPGA or ASIC).

Figure 3B:
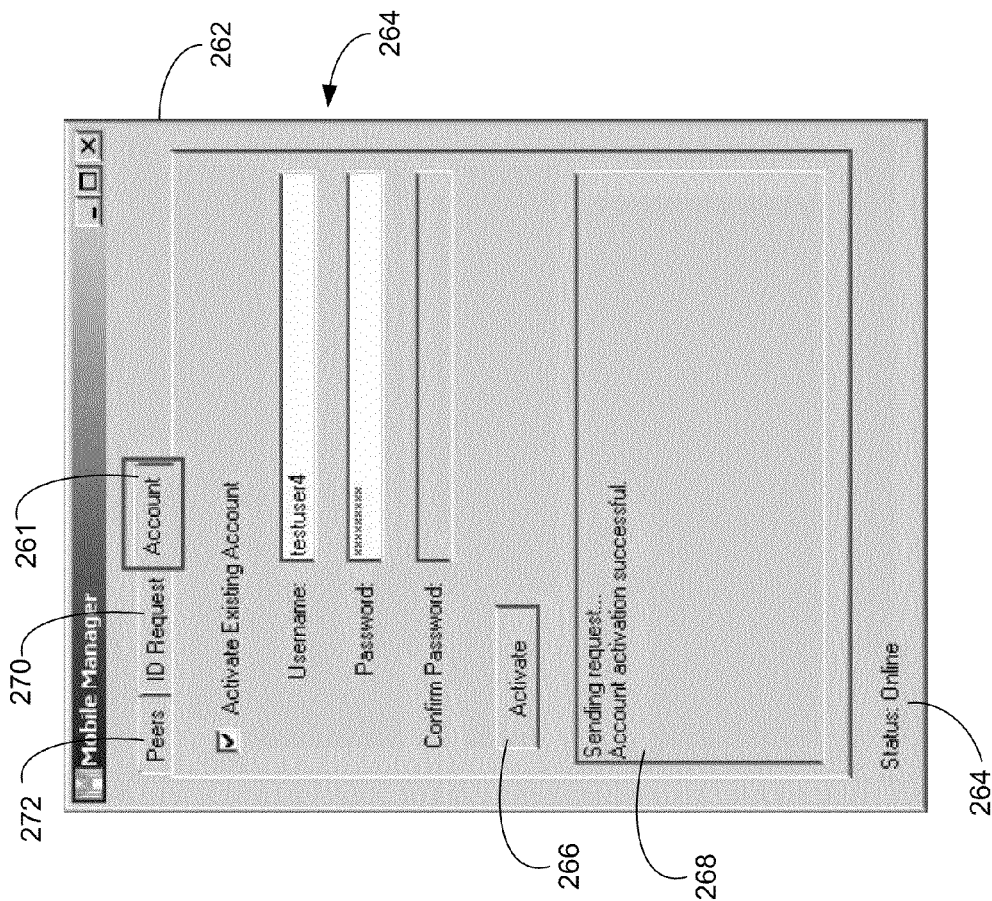
FIG. 3B illustrates a graphical user interface for software being executed on the medical workstation.

FIG. 3B illustrates an account tab 261 of GUI 262 for user interaction with the service application 210. The GUI 262 includes a status indicator 264 that indicates whether a session has been established with the IM server 120. The GUI 262 also includes a login section 264 enabling a user to enter login information. Once the user information is entered into section 264, the user selects the activate button 266, which starts a session with the IM server 120. The GUI 262 also has a log window 268 that displays recent activity by the service application 210. The peers tab 272 and ID request tab 270 will be discussed in greater detail below with respect to FIGS. 5B and 10B, respectively.

In some instances, the medical workstation 110 is a medical image server that is not intended for image viewing but, rather, is intended as a medical image repository that interacts with the IM server 120 and other medical workstations that are intended for image viewing. For example, the medical image server implementation may be an image archive in a PACS.

IM Server

Figure 4:
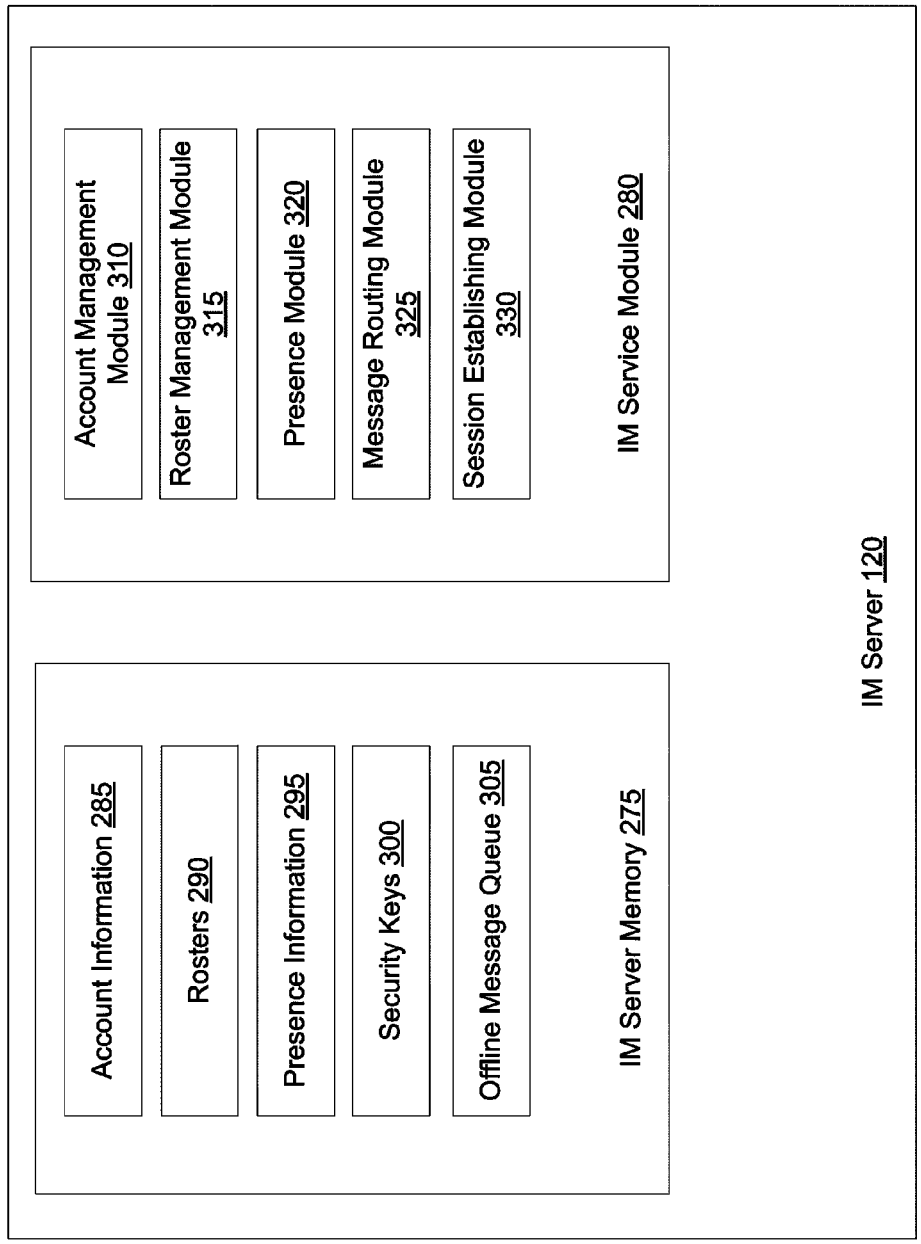
FIG. 4 depicts an IM server for facilitating IM conversations between client devices.

FIG. 4 depicts the IM server 120 according to some embodiments of the invention. The IM server 120 generally handles the flow of messages between client devices of the IM infrastructure, including the remote device 105 and the medical workstation 110. For instance, the IM server 120 maintains a roster for each client device, maintains presence information indicating the availability of each client device, provides certain roster and presence information to appropriate client devices, and routes instant messages between client devices.

To perform these and other functions, the IM server 120 includes an IM server memory 275 and an IM service module 280. The IM server memory 275 includes account information 285, rosters 290, presence information 295, security keys 300, and an offline message queue 305. The IM service module 280 includes an account management module 310, roster management module 315, presence module 320, message routing module 325, and session establishing module 330.

Upon registration of a client device, the account management module 310 creates an account entry within the account information 285. The account entry includes, for instance, a unique identification number (UID) for the client device, a personal identification number (PIN), an email address, a password, a phone number, and a nickname.

A client-specific roster is also created upon registration of each client device and the roster is stored in rosters 290. Each roster within rosters 290 is associated with a client device and is identifiable by the client device's UID. Each roster is initially set up to include the BOT 130 as a contact (also known as a "friend" or "buddy"). The roster management module 315 is used to create, edit, and delete roster information within rosters 290. To add additional contacts to a roster, a secure registration process is used, which is described in more detail below. A roster entry includes the associated client device's UID, a list of UIDs for contacts of that client device, and various permissions or restrictions for each contact.

Figure 5A:
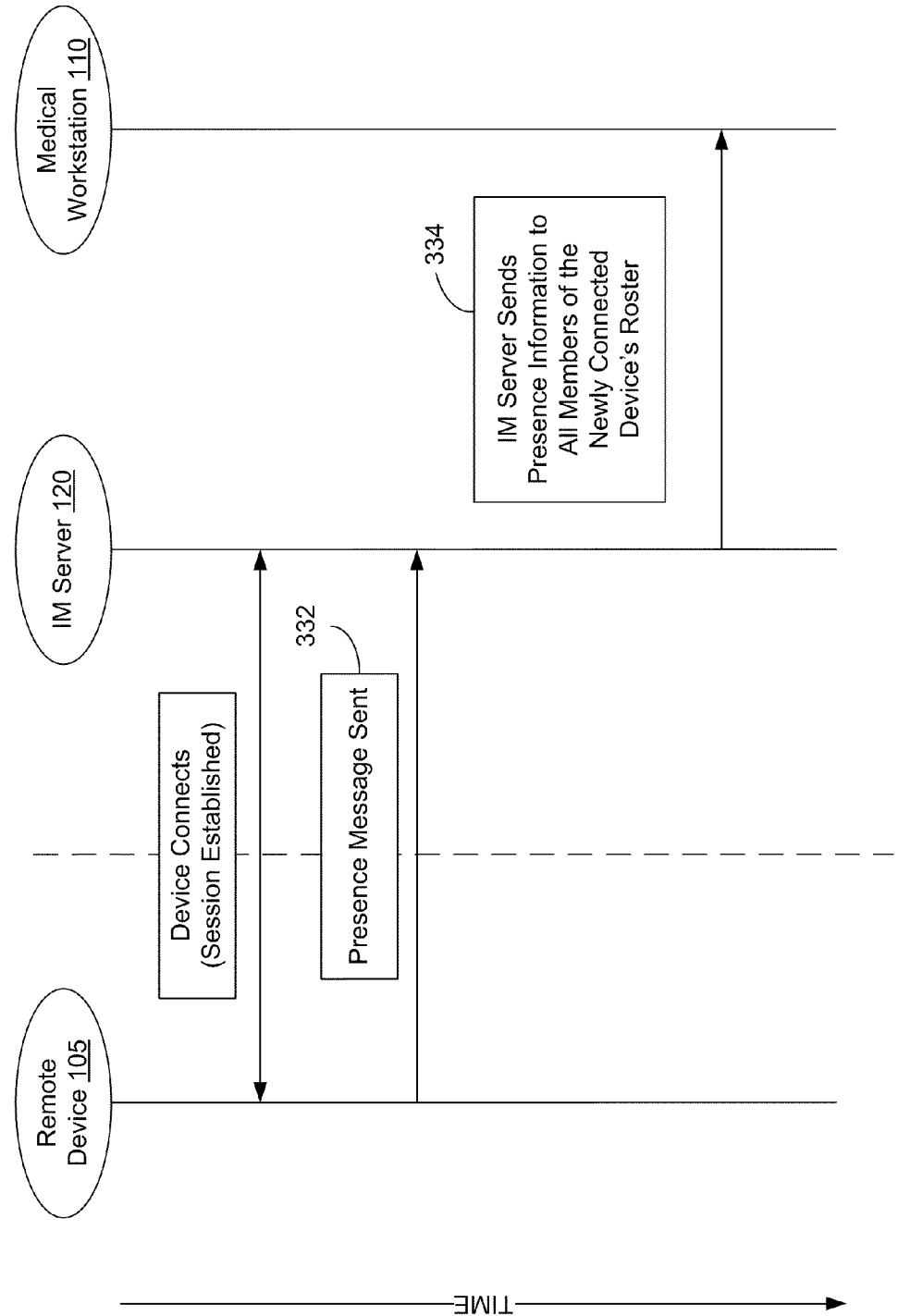
FIG. 5A illustrates a message flow for presence messages.

The presence module 320 maintains presence information 295, which indicates the availability of client devices indexable using their respective UIDs. FIG. 5A illustrates the communications flow of presence messages 332 and 334 between the remote device 105, IM server 120, and medical workstation 110. Upon establishing a session between a client device (e.g., remote device 105) and the IM server 120, the remote device 105 sends a presence message 332 to the IM server 120 (see FIG. 5A). In response, the presence module 320 updates the presence information 295 for the remote device 105. In particular, the entry for the remote device 105 is updated to indicate that the remote device 105 is available for IM communications. The presence module 320 also determines when the session has ended between the IM server 120 and the remote device 105, for example, by receiving a presence message from the remote device 105 or by polling after a predetermined amount of time and not receiving an answer from the remote device 105.

Figure 5B:
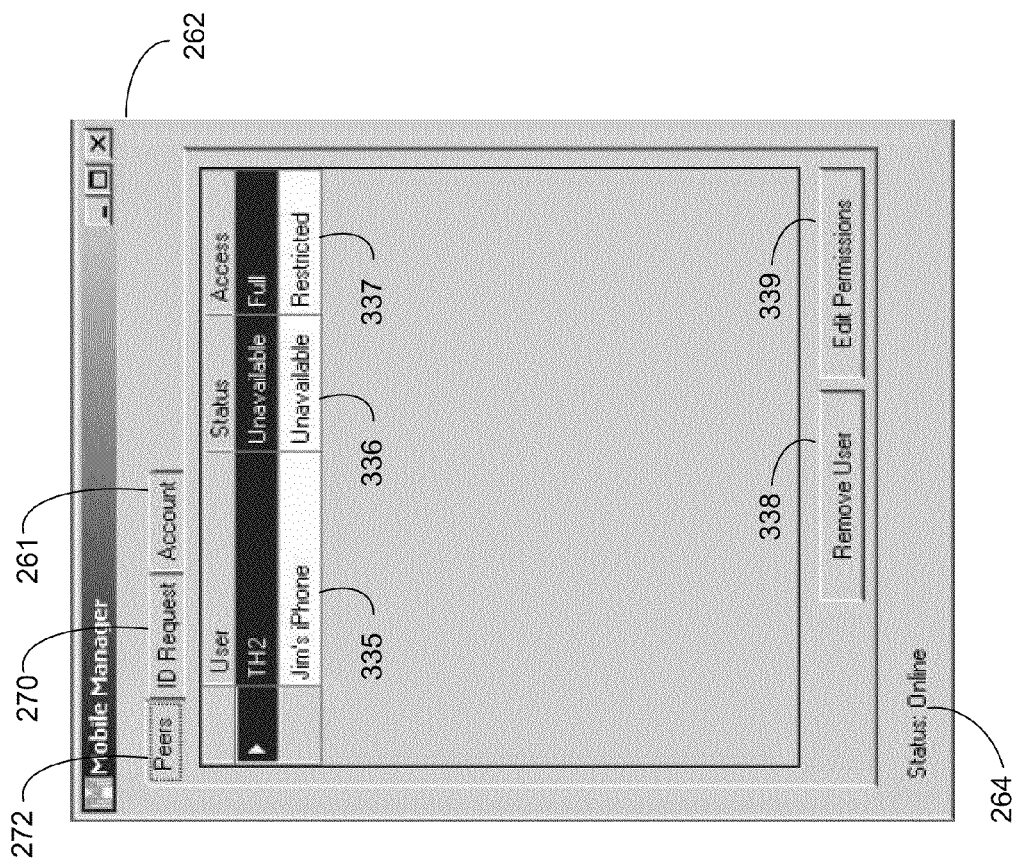
FIG. 5B illustrates a graphical user interface for software being executed on the medical workstation.

The presence module 320 uses the roster management module 315 to retrieve roster information to identify the client devices that should be made aware of particular changes to presence information. For example, the presence module 320 determines which client devices coupled to the IM server 120 have the remote device 105 as a contact on their associated roster within rosters 290. Those contacts identified by the presence module 320 are sent the presence message 334 to indicate a change in presence status of the remote device 105 to available or unavailable. FIG. 5B illustrates the peers tab 271 of GUI 262 on the medical workstation 110. The peers tab 271 lists the roster of the medical workstation 110 and the related presence information. For instance, peers tab 271 includes a contacts column 335 listing the contacts on the roster of the medical workstation 110, a status column 336 listing the presence information for each contact on the roster, and a permissions column 337 listing the permission level assigned to each contact on the roster. A user can also remove contacts from the roster of the medical workstation 110 and edit permission levels using the remove button 338 and edit permissions button 339, respectively, on the peers tab 271.

Turning back to FIG. 3, the security keys 300 include public keys published by client devices. The public keys for each client device are stored in the security keys 300 by the account management module 310 upon registration. As is discussed in greater detail below, the public keys are used by client devices to encrypt and decrypt messages and the identities of message senders.

The session establishing module 330 is used to establish IM communication sessions between the IM server 120 and client devices. For instance, the session establishing module 330 receives initial handshaking messages from the remote device 105 requesting to start a session and identifying itself. The session establishing module 330 then verifies that the remote device 105 is permitted to establish a session by comparing provided information (e.g., UID and password) with data within the account information 285.

The message routing module 325 is responsible for receiving messages from client devices and routing the messages appropriately. For instance, a presence message received from a client device is routed to the presence module 320. A message from one client device (e.g., the remote device 105) addressed to another client device (e.g., to the medical workstation 110) is routed by the message routing module 325 to the addressed recipient (e.g., the medical workstation 110).

The offline message queue 305 is used by the message routing module 325 if the IM server 120 receives a message for an intended recipient that is not available, which is determined via the presence module 320. In the case of an unavailable recipient, the message is temporarily stored in the offline message queue 305 by UID until the intended recipient becomes available. The offline message queue 305 purges messages in the offline message queue 305 if the intended recipient does not become available within a certain amount of time. Upon creation of a session with a client device, the IM server 120 determines whether a message for that client device is being stored in the offline message queue 305 and forwards the message to the client device. In some embodiments, the client device has the responsibility to poll the offline message queue 305 upon creation of a session with the IM server 120.

Registration and Roster Management

Before the IM server 120 will forward messages between two client devices, each client device is registered with the IM server 120 and each device has the other added as a roster contact. A message from a sending client device will not be forwarded by the IM server 120 to a receiving client device unless 1) the sending client device is on the receiving client device's roster and 2) the receiving client device is on the sending client device's roster. A client device works with the web server 125 to create a new account on the IM server 120 and works with the BOT 130 and another client device to add contacts to their associated rosters within rosters 290.

Figure 6:
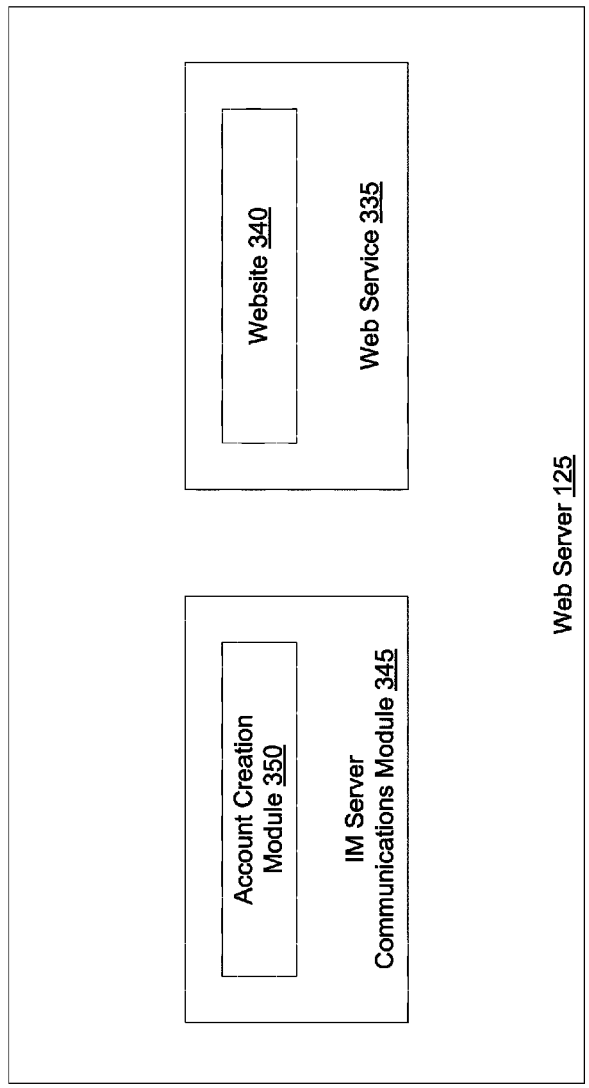
FIG. 6 depicts a web server for creating an account on the IM server.

FIG. 6 depicts the web server 125 according to some embodiments of the invention. The web server 125 is used 1) to register client devices, such as the remote device 105 and medical workstation 110, with the IM server 120 and 2) to alter a client device's roster information stored in rosters 290. The web server 125 includes a web service 335 with website 340 and an IM server communications module 345 with an account creation module 350.

Figure 7:
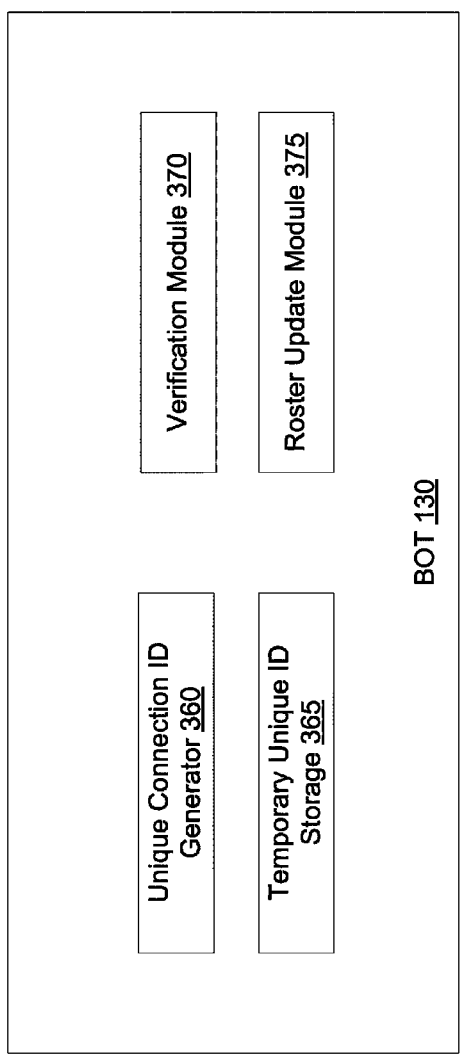
FIG. 7 depicts a remote instant message client (BOT) for updating rosters on the IM server.

FIG. 7 depicts the BOT 130 according to some embodiments of the invention. The BOT 130 is a client device of the IM server 120 and communicates with the IM server 120 according to the IM protocol of the IM server 120. The BOT 130 is included on the roster of each client device in the rosters 290 automatically upon creation of an account for each device. The BOT 130 is used to securely add client devices to rosters to enable communication therebetween. For example, the BOT 130 is used to add the remote device 105 to the roster of the medical workstation 110 and vice versa.

Figure 8:
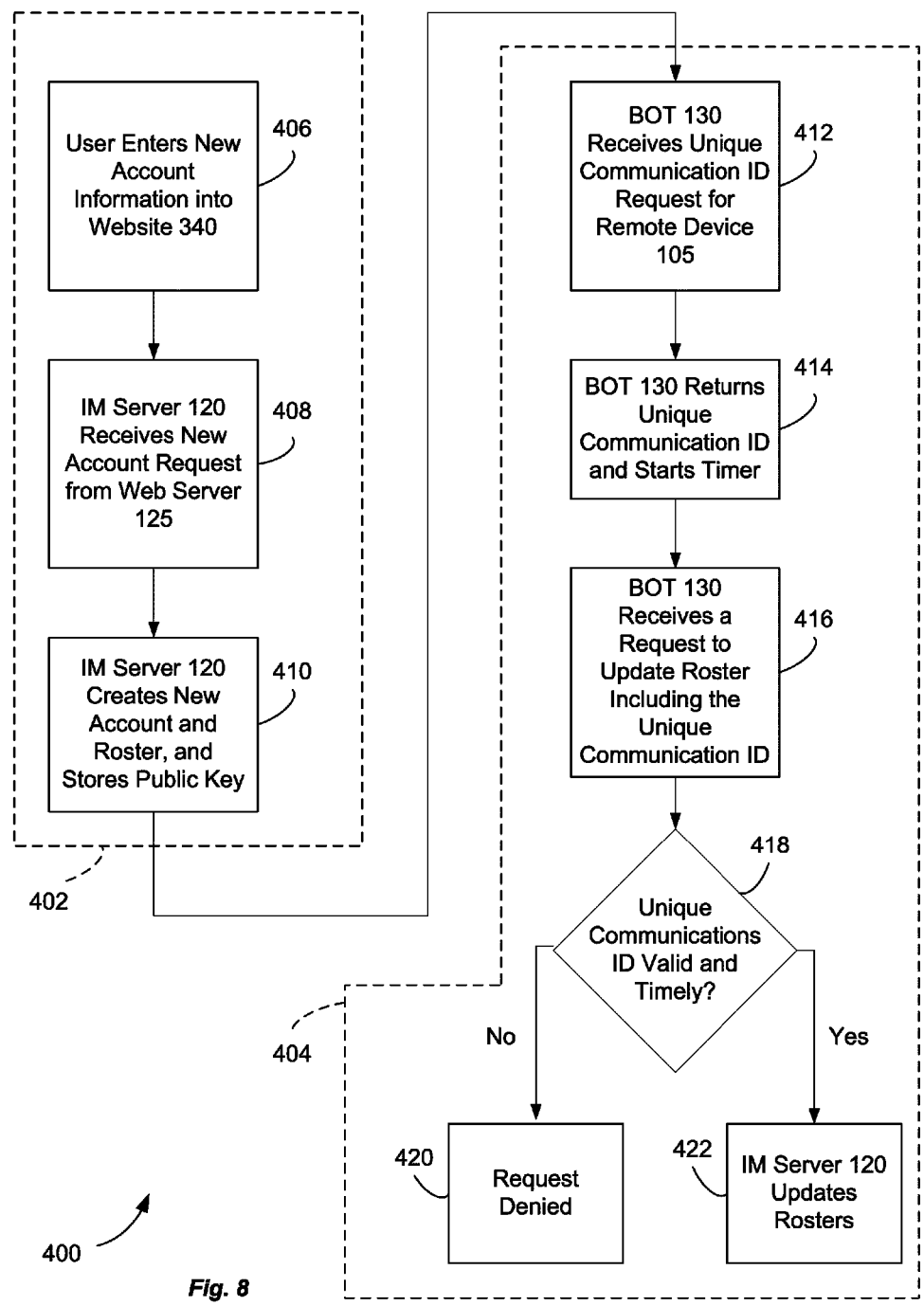
FIG. 8 depicts a method of registering a client device with the IM server and updating the client device's roster.

FIG. 8 depicts a method 400 of registering the remote device 105 using the web server 125 and updating the remote device 105 and medical workstation 110 rosters using the BOT 130. The method 400 is separated into two sub-methods, account creation method 402 and roster update method 404. The method 400 is also applicable to registering other client devices for communications via the IM infrastructure. For example, the method 402 is used for both remote devices, such as remote device 105, and medical devices, such as medical workstation 110. The method 404 is used for updating the rosters of a remote device and medical workstation pair, to enable communications therebetween.

In step 406, a user of remote device 105 enters new account information into the website 340. The website 340 includes a collection of web pages viewable on a web browser, such as web browser 150 and web browser 220. The website 340 displays a form in which a user enters account information for the remote device 105 being registered. The account information includes, for instance, a PIN, email address, password, phone number, and a nickname for the remote device 105.

The web service 335 of the web server 125 enables the website 340 to be accessible at a website address (i.e., at a uniform resource locator (URL) address). The website address is supplied to potential client devices including the remote device 105. In some instances, the website address is pre-loaded into the client IM application 145 and a user is able to select a register button via the GUI of the remote device 105, which causes the launch of the web browser 150 and display of the website 340. In other instances, a user manually types the website address into the web browser 150 to load the website 340. In still other instances, a user accesses the website 340 with a web browser on a computer independent of the remote device 105, although some modifications to the method 402 may be needed. For example, the independent computer will provide some of the data generated during the method 402 to the remote device 105.

Also in step 406, the remote device 105 generates a public/private key pair. The private key is stored locally on the remote device 105 and the public key is sent to the web server 125 as part of the account information.

In step 408, the IM server 120 receives a new account request from the web server 125. The new account request includes account information entered via the website 340 (the user-entered account information). The account creation module 350 communicates the user-entered account information to the account management module 310 of the IM server 120.

In step 410, the account management module 310 uses the received user-entered account information to generate a new UID and to create a new account entry within the account information 285. Also in step 410, the public key of the remote device 105 is stored in security keys 300. Additionally in step 410, the roster management module 315 creates a new roster for the UID and includes a UID of the BOT 130 as a contact on the new roster. Upon successful creation of an account and roster, the IM server 120 communicates a confirmation message to the web server 125, which forwards the confirmation to the remote device 105. For instance, the confirmation is displayed on the website 340 for viewing by the user on the web browser 150.

In addition, the account information, including the private key, is stored locally on the remote device 105. Before being stored, this account information is encrypted using the PIN. In some embodiments, the encrypting and local storing occurs in step 406 rather than step 410.

Figure 9A:
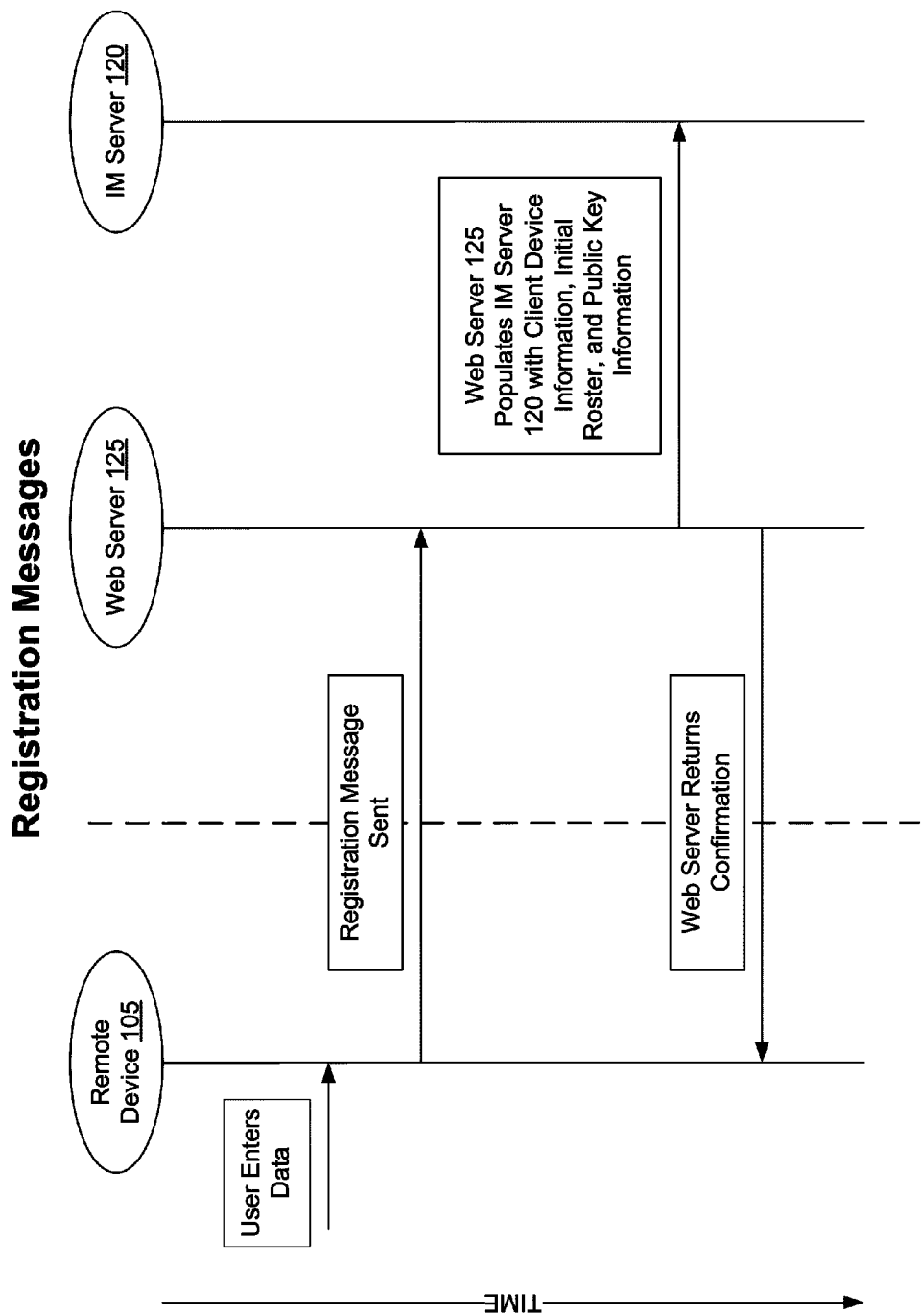
FIG. 9A illustrates a message flow for creating a new account.

FIG. 9A illustrates communications between the remote device 105, IM server 120 and web server 125 used to complete the account creation method 402. Although described with respect to remote device 105, the account creation method 402 is also applicable to adding accounts for other client devices, such as medical workstation 110.

Figures 9B, 9C:
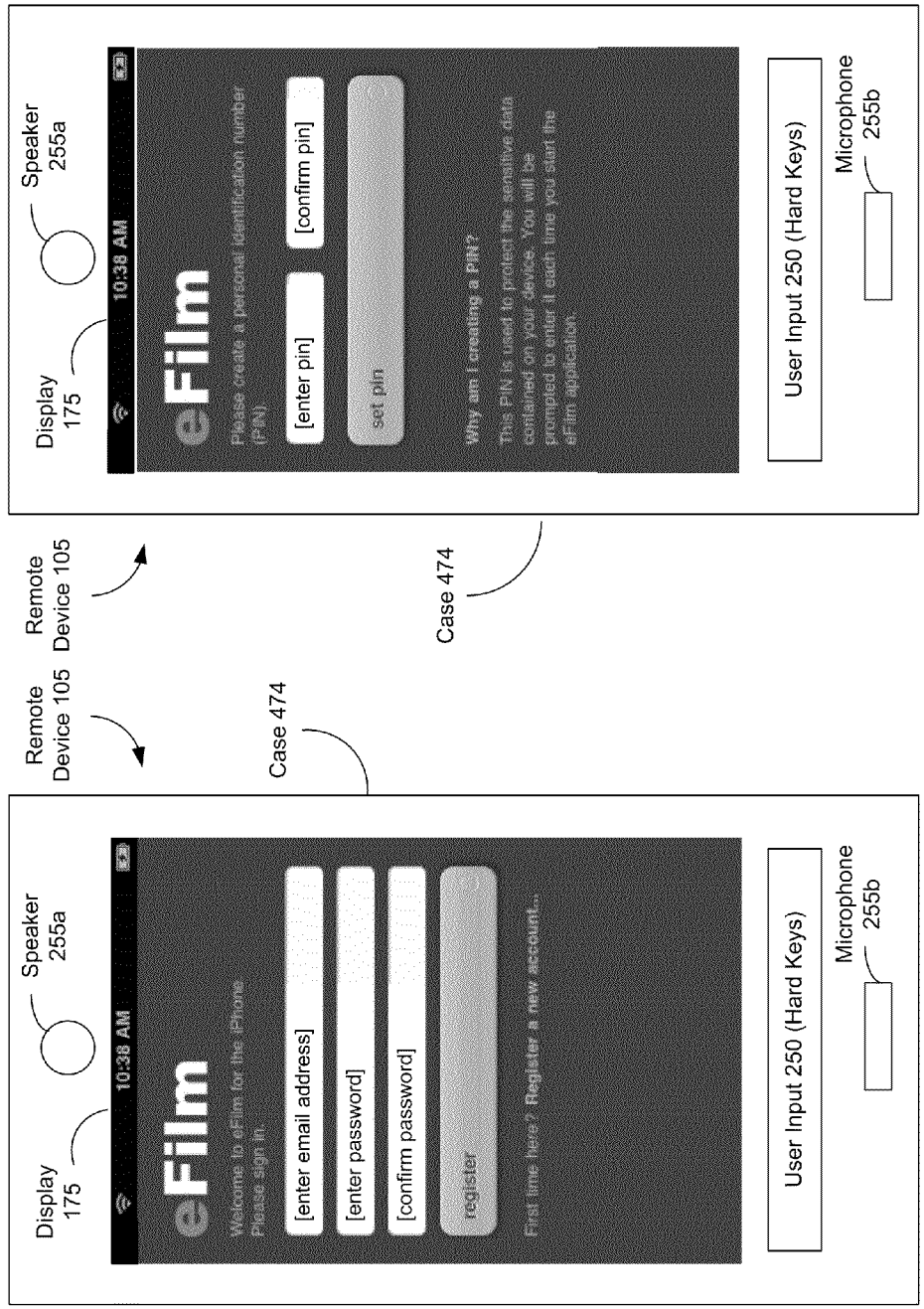
FIGS. 9B-C illustrate a graphical user interface for software being executed on the remote device.

In some embodiments, the remote device 105 communicates with the website 340 and web server 125 without using web browser 150. For instance, the client IM application 145 provides a GUI for a user to input registration information and communicates the registration information to the web server 125. FIGS. 9B and 9C illustrate screen shots of an exemplary GUI for receiving user registration information. In some instances, the registration information is sent over multiple messages from the remote device 105 to the web server 125. For example, a first message includes a user name, password, and email address, while a second message includes a PIN.

Roster Update

Figure 10A:
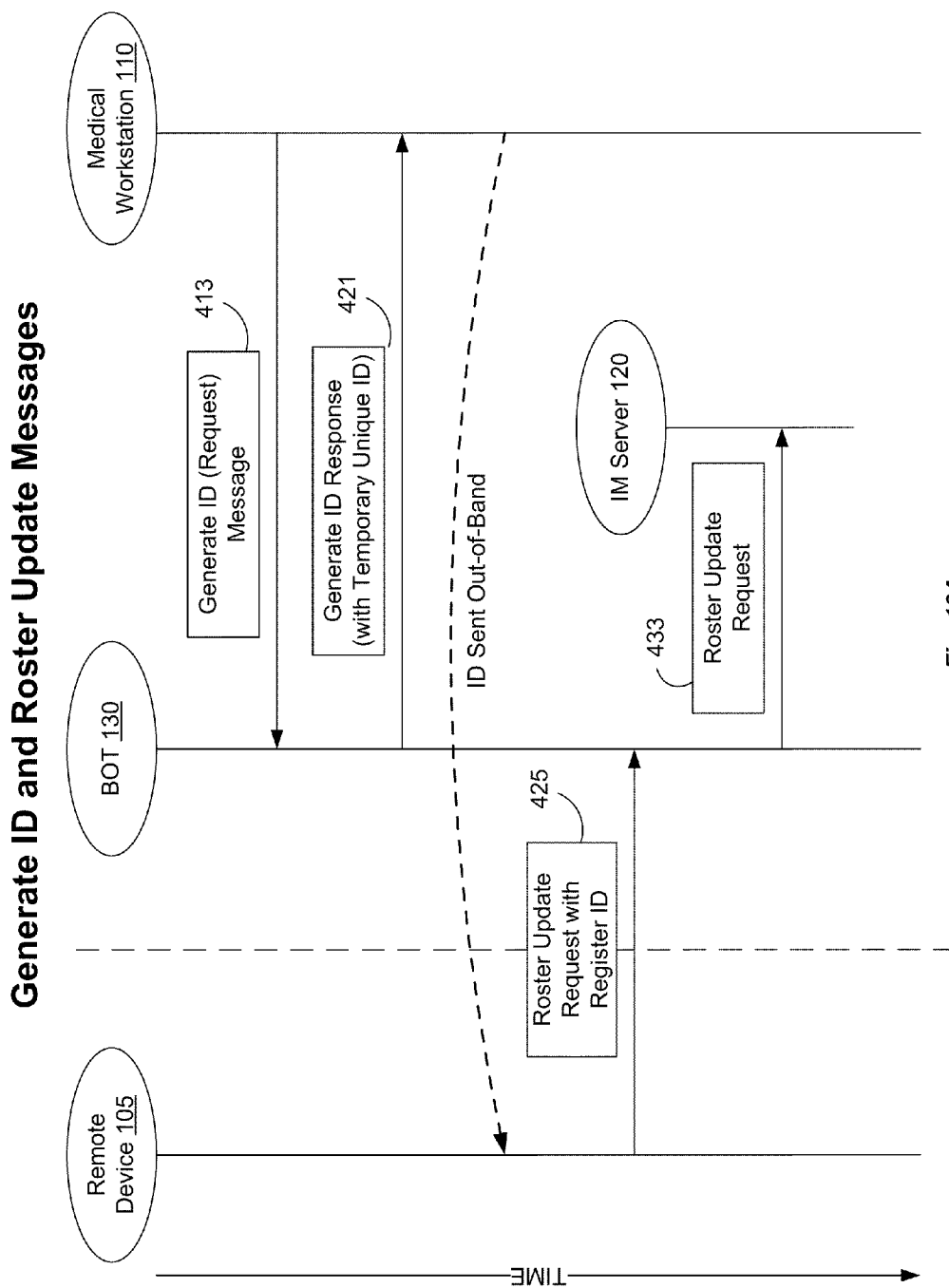
FIG. 10A illustrates a message flow for updating a roster.

After creation of its account on the IM server 120, the remote device 105 includes BOT 130 as a contact on its rosters within rosters 290. However, the remote device 105 and medical workstation 110 are not listed as contacts on each others' rosters and, therefore, are not yet able to exchange instant messages via the IM server. The roster update method 404 of FIG. 8 includes steps used to add the remote device 105 to the medical workstation 110 rosters and vice versa. FIG. 10A illustrates the communications between the remote device 105, medical workstation 110, IM server 120, and BOT 130 used to complete the roster update method 404 of FIG. 8.

Figure 10B:
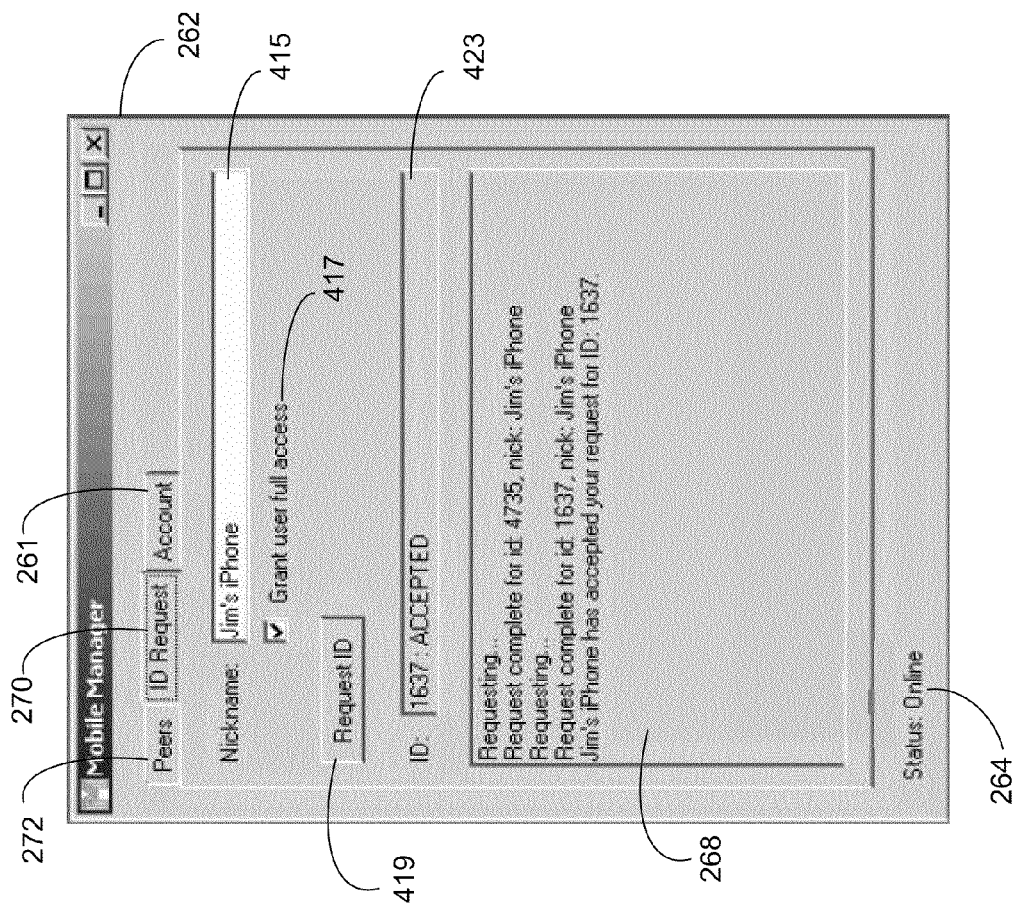
FIG. 10B illustrates a graphical user interface for software being executed on the medical workstation.

In step 412, the BOT 130 receives a request from the medical workstation 110 for a unique connection ID (generate ID message 413). For instance, a user or another individual present at the medical workstation 110 uses the service application 210 to request a unique connection ID. The service application 210 GUI provides a form for entering a nickname of the medical workstation 110 and specifying access rights for the remote device 105, and a request button that submits the request upon activation (e.g., using a mouse click). For instance, FIG. 10B illustrates the ID request tab 270 of the GUI 262. On the ID request tab 270, a user at medical workstation 110 can enter a nickname in box 415, set a permission level using check box 417, and request an ID using the request ID button 419 for the remote device 105.

In response to the request, the BOT 130 uses the unique connection ID generator 360 to generate a unique connection ID with a set lifespan (e.g., ten minutes). The BOT 130 stores the generated unique connection ID with the UID of the requesting medical workstation 110 and the set lifespan in the temporary unique ID storage 365. The lifespan may be stored by calculating and storing the absolute end time of the unique connection ID (e.g., 10:33 am) or by storing the creation time (e.g., 10:23 am) and the duration of the lifespan (e.g., ten minutes).

In step 414, the BOT 130 replies to the medical workstation 110 with a generate ID response message 421 including the generated unique connection ID and the lifespan. The medical workstation 110 then displays the generated unique connection ID and the lifespan on display 245. For instance, the ID request tab 270 of FIG. 10B includes an ID display 423 that displays the generated unique connection ID. In some instances, the lifespan is displayed as a timer that counts down the remaining time of the lifespan. The generated unique connection ID and nickname are provided to a user of the remote device 105 via some other out-of-band communication in addition to or in place of displaying them on the display 245. An out-of-band communication is a communication that occurs independent of the IM server 120, such as an email, phone call, text message, etc.

Figure 10C:
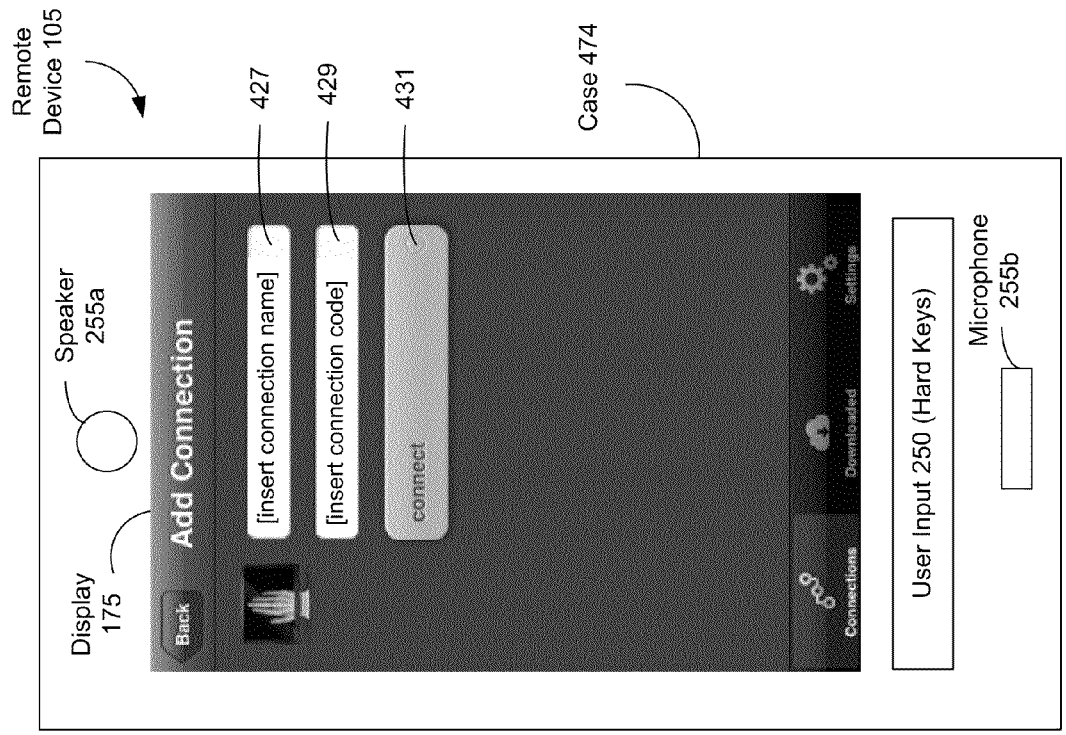
FIG. 10C illustrates a graphical user interface for software being executed on the remote device.

In step 416, the remote device 105 sends a register ID message 425 to the BOT 130 requesting a connection to the medical workstation 110. The request message includes the generated unique connection ID and a nickname to describe the medical workstation 110. FIG. 10C illustrates an exemplary GUI for remote device 105 used to enter a nickname for the medical workstation 110 and the generated unique connection ID in boxes 427 and 429 respectively. After entering the nickname and generated unique connection ID, a user selects the connect button 431 to cause the remote device 105 to generate and send the register ID message 425 to the BOT 130.

In step 418, the verification module 370 of the BOT 130 determines whether the unique connection ID and nickname match an entry within the temporary unique ID storage 365. The verification module 370 also determines whether the lifespan of the unique connection ID has expired in step 418. If the verification module 370 cannot verify the existence of a matching entry or an unexpired lifespan for the unique connection ID, it returns a failure message to the remote device 105 in step 420. Upon verification of a matching entry and an unexpired lifespan, however, the BOT 130 sends a roster update request message 433 to the IM server 120 to update rosters 290 in step 422. In step 422, the roster update module 375 is used to communicate with the roster management module 315 of the IM server 120 to update rosters 290. In particular, the roster of the remote device 105 is updated to include the medical workstation 110 and the roster of the medical workstation 110 is updated to include the remote device 105. In some instances, the BOT 130 or the IM server 120 sends a confirmation message indicating that the roster update was successful. Thereafter, the remote device 105 and medical workstation 110 are operable to communicate with each other using instant messages via the IM server 120.

The BOT 130 communicates with the roster management module 315 using instant messages according to the IM protocol of the IM server 120. In some instances, however, the BOT 130 has the ability to directly manipulate the rosters 290. Although the BOT 130 is depicted as an independent computing device in FIG. 1, the BOT 130 is deployed in the web server 125 or IM server 120 in other embodiments.

During the roster update performed by the BOT 130, the remote device 105 is assigned one of two permission/access levels, full access or limited access. The user at the medical workstation 110 chooses which permission level to assign the remote device 105. With full access, the remote device 105 is able to obtain and transfer any image in the medical image database 235 of medical workstation 110. With limited access, the remote device 105 has access to no image data by default. Instead, access to images are granted by the medical workstation 110 (e.g., via service application 210) on a patient-by-patient basis or image-by-image basis, for example. In some instances, other permission levels can be assigned to the remote device 105. For instance, various permission levels can be used to selectively enable and disable features (e.g., moving images between workstations).

IM Protocol

After registering the remote device 105 and medical workstation 110 and adding each device on the other's roster as a contact, the devices are able to communicate via the IM server 120. Communications within system 100 occur in "conversations" between two client devices, such as between the remote device 105 and medical workstation 110. The conversations include transfers of text and data that conform to an IM protocol of the IM infrastructure. The conversations are used, for instance, by the remote device 105 to query and control the medical workstation 110 using instant messages.

In embodiments of the invention, the conversations between client devices occur in the background out of a user's view. For instance, the client IM application 145 GUI on the remote device 105 provides a user-friendly interface for navigating the medical image database 235 of the medical workstation 110. When a user selects a particular image, queries the medical workstation 110, or takes some other action on the GUI that requires interaction with the medical workstation 110, the client IM application 145 generates an instant message that is sent to the medical workstation 110 via the IM server 120. The instant message is not viewable by the user of the remote device 105 or the medical workstation 110. Rather, the instant message is transparent to the user. The instant message is generated in the background by the client IM application 145 and is received and acted upon by the service application 210 (via the API 215). Thus, no "chat window" or the like is generally displayed for the user of the remote device 105 to converse with the medical workstation 110. Additionally, unlike some instant messaging systems, users are not made aware of their associated instant messaging account information. In some embodiments, however, users are made aware of their associated instant messaging account information.

The messages communicated between the remote device 105 and the medical workstation 110 follow an IM protocol of the IM server 120. In some embodiments, the IM protocol is an enhanced version of the Extensible Messaging and Presence Protocol (XMPP) protocol including both standard XMPP message formats and new message formats. The IM protocol includes several message types including: presence messages, generateID/registerID messages, roster messages, publish/subscription messages, query messages, get destinations messages, image move messages, and image retrieve messages. The presence messages 332 and 334 were described above with respect to FIG. 5A and the generated/registerID messages (generate ID message 413, generate ID response message 421, register ID message 425, and roster update request message 433) were described above with respect to FIG. 10A and the roster update method 404.

In addition to the public and private key secure communications described below, an additional layer of secure communication occurs by use of a Transport Layer Security (TLS) or Secure Sockets Layer (SSL) cryptographic protocol. The TLS and SSL protocols allow applications on the remote device 105, IM server 120, medical workstation 110, web server 125, and BOT 130 to communicate across the network 115 in a way designed to prevent eavesdropping and tampering. The TLS and SSL protocols provide security for communications over the networks 115 by encrypting segments of network 115 connections at an application layer to ensure secure end-to-end transit at the transport layer. Thus, even for those messages that may not be encrypted and signed as described below (e.g., a presence message), the messages may be securely communicated using the SSL or TLS protocol. For those messages that are encrypted and signed as described below (e.g., a query message), the messages may be securely communicated using the SSL or TLS protocol as an additional layer of security.

Request Roster Messages

The roster messages used in the system 100 may be similar to XMPP roster messages. Roster messages are generated and sent by client devices, such as the remote device 105 or medical workstation 110, to determine which contacts of the client device are available for communication. The client devices are operable to send roster messages to the IM server 120 automatically (e.g., after a session is started) and periodically.

Figure 11A:
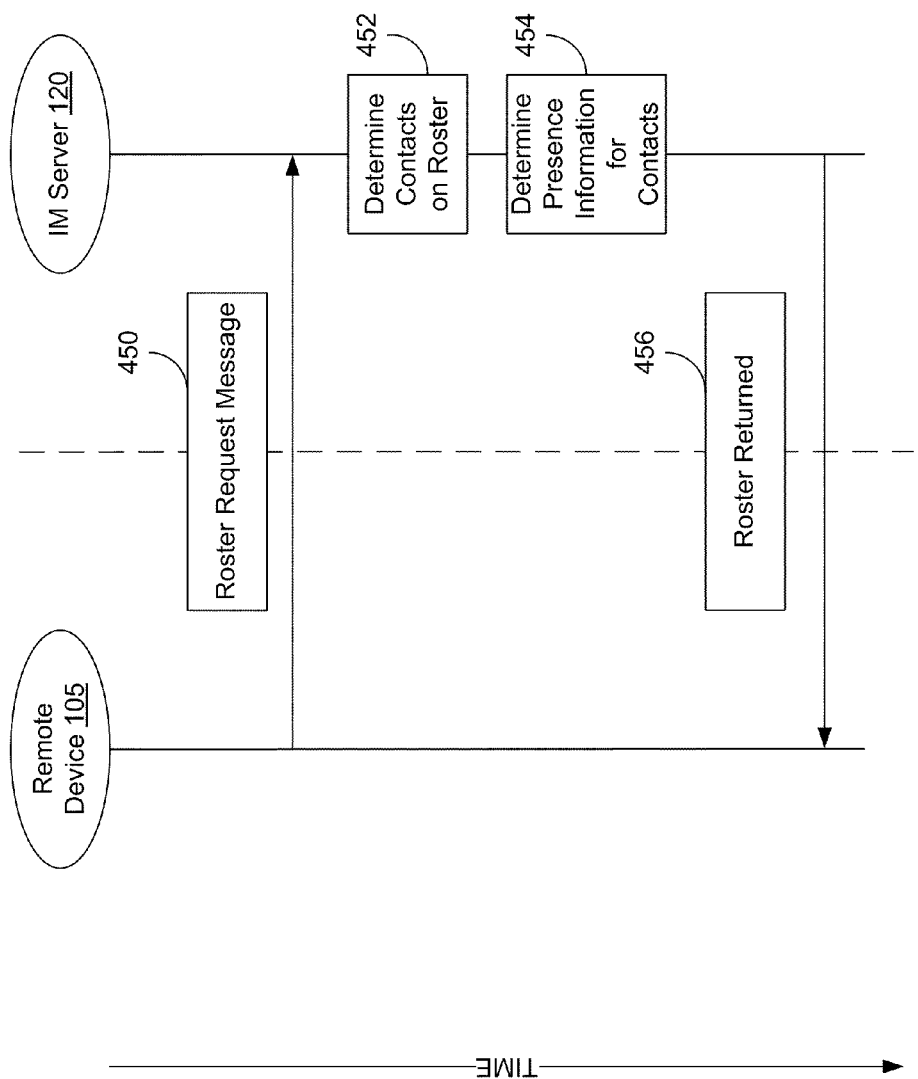
FIG. 11A illustrates a message flow for requesting a roster.

The communication flow for roster messages between the remote device 105 and the IM server 120 is depicted in FIG. 11A. The remote device 105 generates and sends to the IM server 120 a roster request message 450. The roster management module 315 accesses the roster of the remote device 105 within the rosters 290 to determine which client devices are listed as contacts on the particular roster (step 452). Thereafter, the presence module 320 obtains the presence information from the presence information 295 for each listed contact (step 454). The IM service module 280 then generates a response roster message 456 including the contacts of the remote device 105 and their associated presence information (i.e., availability).

Figure 11B:
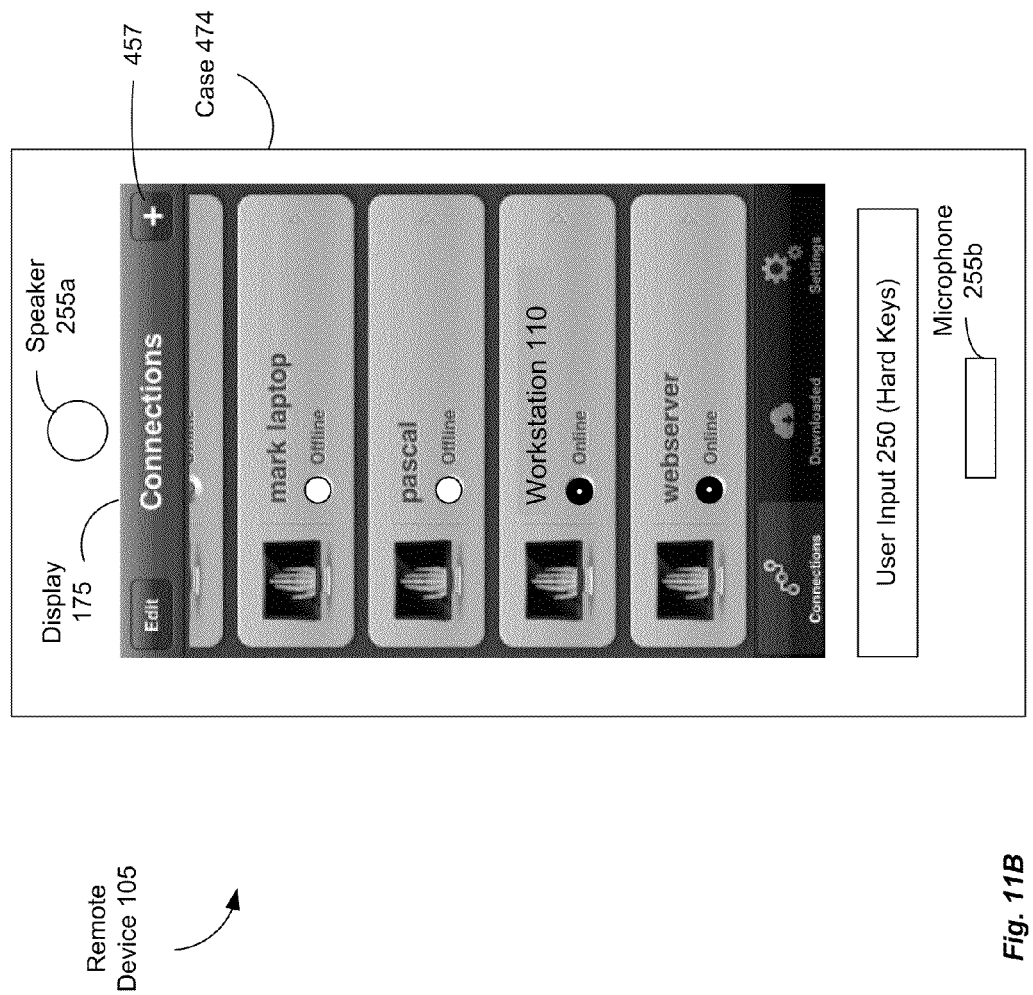
FIG. 11B illustrates a graphical user interface for software being executed on the remote device.

The response roster message 456 is communicated to the remote device 105. The client IM application 145 is then operable to display on the display 175 a list of available and/or unavailable contacts of the remote device 105. FIG. 11B illustrates an exemplary GUI screen for the remote device 105 that is used to display roster information returned from the IM server 120 in the response roster message 456. Each contact on the roster of the remote device 105 (except the BOT) is displayed and a scrolling action allows a user to view contacts that do not fit onto the display 175. Each contact includes an indicator to indicate the contact's availability. For instance, in FIG. 11B, medical workstation 110 and "webserver" are available while "mark laptop" and "pascal" are not available. The GUI in FIG. 11B also includes an add contact button 457, which brings a user to the screen of FIG. 10C.

Subscription and Publication Messages

As noted above, each client device generates a public/private key pair when registering with the IM server 120. The private key is stored locally on the client device (e.g., in security keys 165 or security keys 230) and the public key is stored in the IM server 120 in security keys 300. The public/private key pair is part of a public-key cryptographic infrastructure used for secure data transfers between client devices. In public-key cryptography, a private key is kept secret by one user and the public key may be made widely available. Messages are encrypted with the intended recipient's public key and can only be decrypted with the corresponding private key. In the context of system 100, the remote device 105 obtains a public key for the medical workstation 110 and vice versa. A message from the medical workstation 110 to the remote device 105 is encrypted by the medical workstation 110 with the public key of the remote device 105. Upon receipt of the message, the remote device 105 decrypts the message using the secret private key. If the encrypted message is intercepted, it cannot be read as the intercepting device will not have the private key necessary for decryption. Other cryptographic approaches are used in some embodiments of the invention to maintain secure communications between the remote device 105 and medical workstation 110.

Additionally, certain messages include a digital signature encrypted with the sender's private key (also referred to as a certificate). The recipient uses the sender's public key to decrypt the signature and verify the authenticity of the message's origin. In some embodiments, the public keys are published, retrieved, and managed using the XMPP Extension XEP-0189: Public Key Publishing. Per XEP-0189, the certificates are X.509 certificates and are encoded according to Distinguished Encoding Rules (DER).

Figure 12:
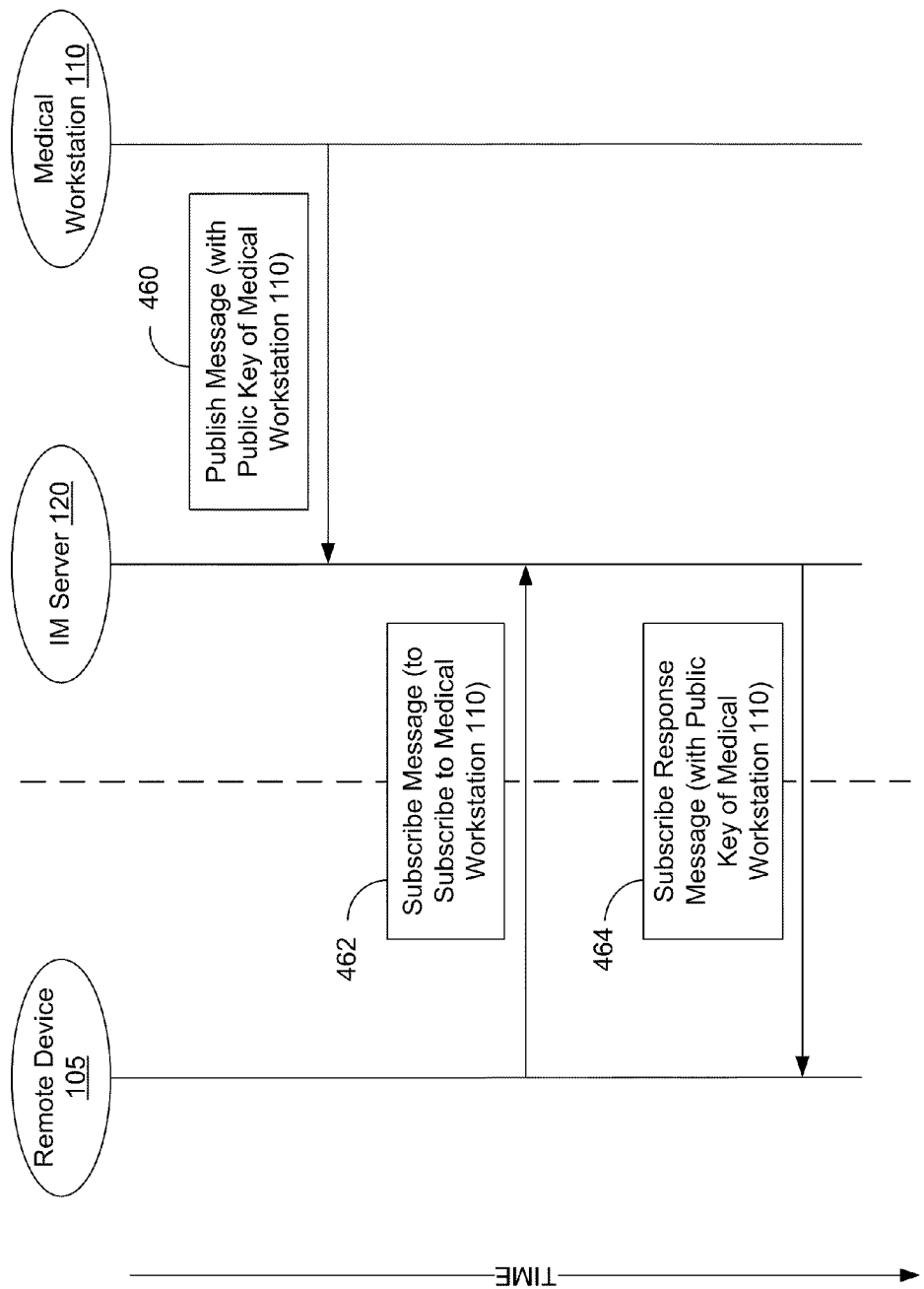
FIG. 12 illustrates a message flow for subscription and publication messages.

The publish/subscription messages enable client devices to publish their public keys to the IM server 120 and to determine their contacts' published public keys. FIG. 12 illustrates the communication flow for a publication message sent by the medical workstation 110 and a subscription message sent by the remote device 105. A publish message 460 including a public key is sent from the medical workstation 110 to the IM server 120. The IM server 120 stores the public key within the security keys 300 portion of the IM server memory 275. In some instances, a confirmation message is returned to the medical workstation 110.

Thereafter, the remote device 105 sends a subscribe message 462 to the IM server 120 requesting to subscribe to the medical workstation 110. The IM server 120 adds a subscription entry to the IM server memory 275 that notes the subscription of the remote device 105 to the medical workstation 110 (e.g., using each device's UID). The subscription entry is stored in rosters 290 in some instances. The IM server 120 sends a subscribe response message 464 to the remote device 105 with the public key of the medical workstation 110. If the medical workstation 110 later publishes a new public key to the IM server 120, the IM server 120 will send the new public key to the remote device 105.

The publish message is automatically sent during registration of a client device in step 406 of method 402. The subscription message is automatically sent to the IM server 120 while adding a contact in the roster update method 404. In some instances, the BOT 130 generates the subscription message on behalf of a client device. In other instances, the client device sends the subscription message during or after the roster update method 404.

Query Messages

The query message is used by the remote device 105 to determine the images on the medical workstation 110 that are available to the remote device 105. In some embodiments, after the remote device 105 creates a session with the IM server 120, the GUI of the client IM application 145 lists the available contacts, including the medical workstation 110. Upon selection of the medical workstation 110, a user is able to specify a query message 470 to be generated by the client IM application 145. For instance, after selecting the medical workstation 110, the GUI of the client IM application 145 displays at least two options: a study list and a series list. If a user selects the study list, the query message 470 with default settings is generated and sent to the medical workstation 110 automatically. Default settings may include, for instance, a limit to the number of results desired, a request for results by date (e.g., most recently added to the medical workstation 110), and/or restrictions for only certain image types (e.g., x-ray image). In other instances, the user has an opportunity to alter or add to the default settings before the query message 470 is generated and sent. For example, the user can specify a patient identifier (name, ID, etc.), patient characteristics (sex, age), and a date/time of the image. Additionally, the user is operable to enter key words that are used as search terms to search a description of the image or other image/patient characteristics.

The query message 470 is encrypted with the medical workstation's public key, and a digital signature encrypted with the private key of the remote device 105 is included. In some instances, the query message with default settings is sent automatically upon selection of the medical workstation 110.

Figure 13:
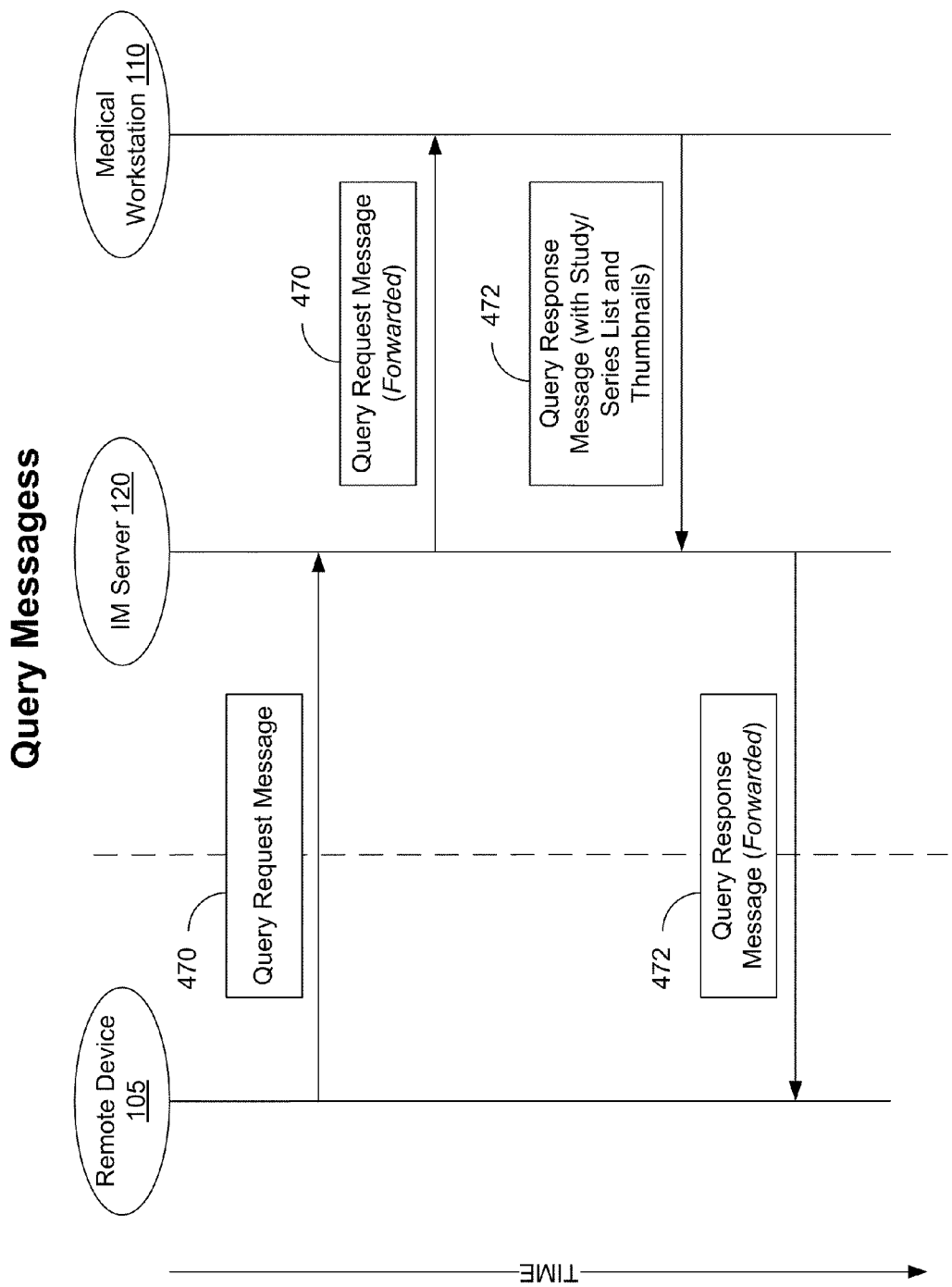
FIG. 13 illustrates a message flow for query messages.

FIG. 13 illustrates the communication flow for the generated query message 470 sent from the remote device 105 to the medical workstation 110 via the IM server 120. The remote device 105 sends the query message 470 to the IM server 120. The message routing module 325 forwards the query message 470 to the medical workstation 110. The medical workstation 110 verifies that it has the remote device 105 as a contact on its roster. In some embodiments, the IM server 120 performs the roster verification.

The API 215 and service application 210 of the medical workstation 110 verify the digital signature and decrypt the query message 470. The service application 210 also verifies that the remote device 105 has permission to receive a response to the particular query message 470. If so, the service application 210 performs a search of the medical image database 235 and generates an image results list according to the specifics of the query message 470. In some instances, the image results list includes thumbnails or other visual representations of the images. In other instances, the image results list includes a textual description of each image (e.g., patient name, image date, image type, etc.).

The service application 210 and API 215 generate a query response message 472 including the image results list. The query response message 472 also includes an indication of whether there are more image results than allowed by the numeric limit of the query message 470. The query response message 472 is then encrypted using the public key of the remote device 105 and a digital signature encrypted with the private key of the medical workstation 110 is included. The encrypted and signed query response message 472 is sent to the IM server 120, which forwards the query response message 472 to the remote device 105.

The remote device 105 verifies the signature of the query response message 472 and decrypts the message using the public key of the medical workstation 110. The GUI of the client IM application 145 displays the image results list in whole or in part. For instance, the remote device 105 displaying the image results list is illustrated in FIG. 14A. The remote device 105 includes an outer case 474, speaker 255a, and microphone 255b, and is displaying a study list 475 listing four studies. The study for patient 3 includes a "local" identifier indicating that the study was previously obtained and is stored locally on the remote device 105. Therefore, a local identifier indicates that images are viewable without needing to execute additional steps to obtain them from the medical workstation 110.

Upon selection of a study from the study list 475, a new query message is sent to the medical workstation 110, similar to query message 470, that requests the series associated with the selected study. The medical workstation 110 responds with a query response message, similar to query response message 472, including a list of the series associated with the selected study and a thumbnail image for each series. For example, in FIG. 14B, the remote device displays the series list associated with the patient 1 study from study list 475. The patient 1 study includes four associated series and, therefore, four image thumbnails 476-479 are displayed. Thumbnail 477 has a "local" identifier attached to indicate that the study was previously requested and is already stored locally on the remote device 105. Additional items in the results list that are not visible are accessible via a scrolling action. Beneath each thumbnail is a brief description of the image associated with the thumbnail. In some embodiments, text replaces thumbnails 476-479 and other information may be provided for each series item.

Figure 14C:
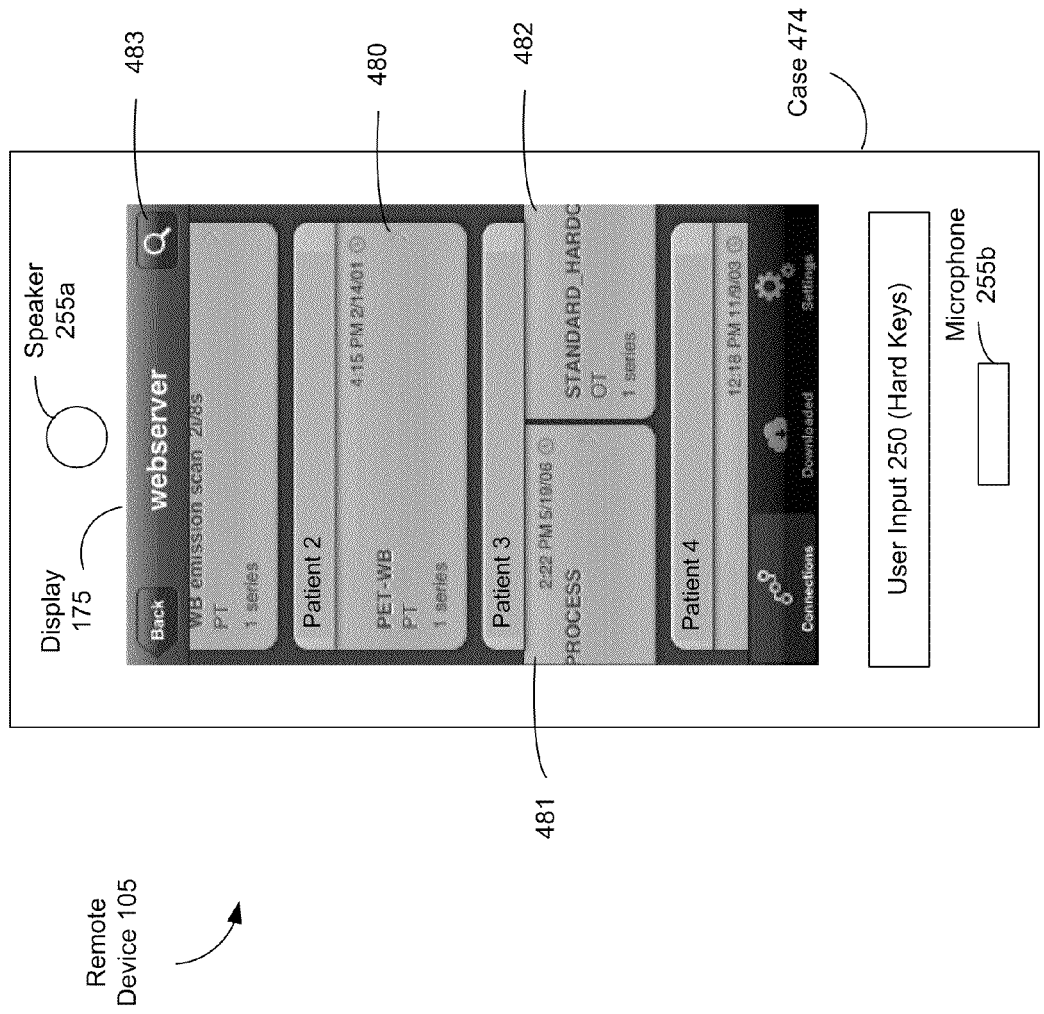
FIGS. 14C-D illustrate a graphical user interface for software being executed on the remote device.

FIG. 14C illustrates an exemplary GUI screen for the remote device 105 that is used to display study information provided by the IM server in a query response message 472. The studies are grouped by patient. If a patient has more than one study, such as patient 3, a user can scroll left and right between that patient's studies while the other patients remain in the same vertical position. For instance, remote device 105 of FIG. 14C is displaying one study for patient 2 (study 480) while the user is moving between two different studies of patient 3 (studies 481 and 482).

Figure 14D:
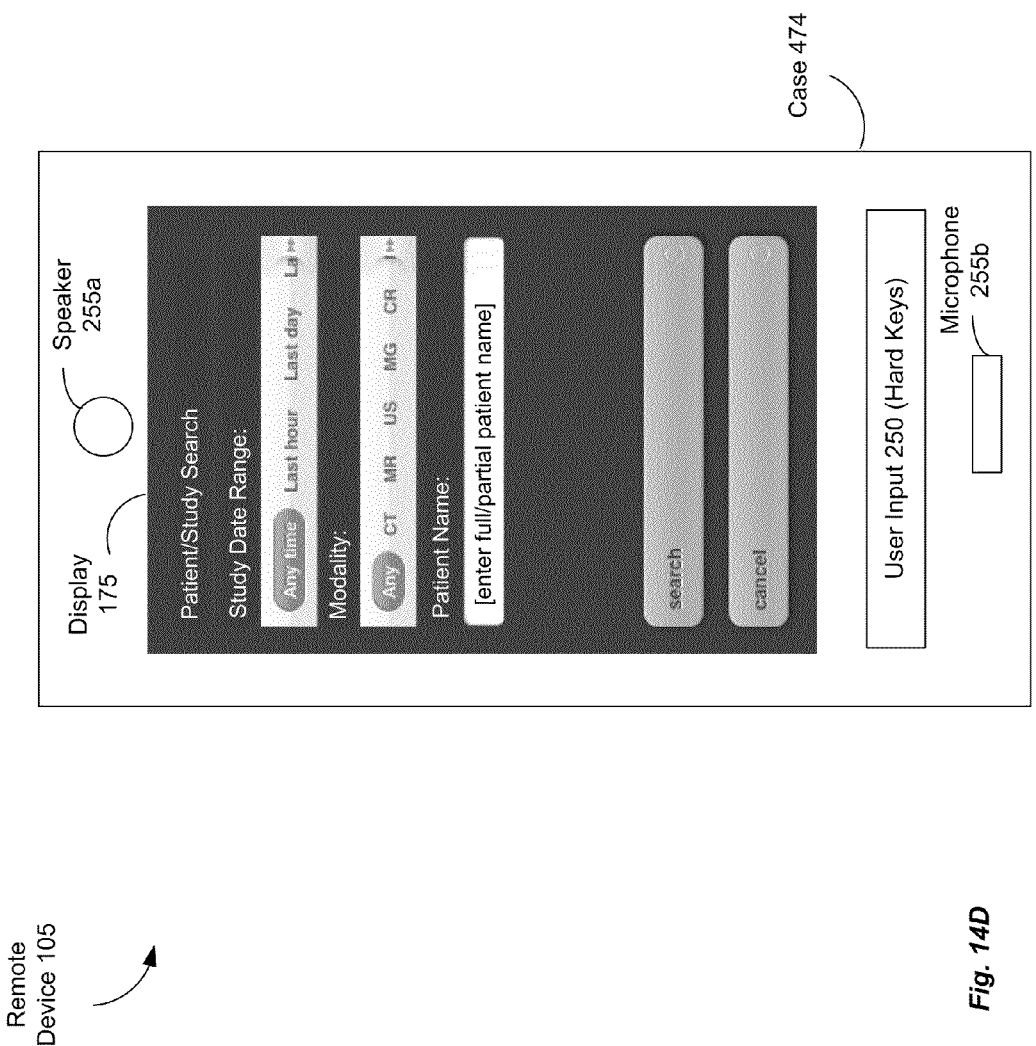

The GUI in FIG. 14C also includes a search button 483, which causes the GUI screen of FIG. 14D to be displayed. FIG. 14D illustrates an exemplary GUI screen for the remote device 105 that is used to search the images within a remote medical image database, such as medical image database 235. A user can specify three search criteria in the GUI screen of FIG. 14D: study date range, modality, and patient name. The results of such a search may be displayed similar to the studies shown in FIG. 14C.

A user is also able to generate a query message for a series without first generating a query for a study list and selecting a study. Similar to the default query message to obtain the available studies on the medical workstation 110, a default query message to obtain the available series on the medical workstation 110 is also generated and sent by the remote device 105 in accordance with a user command. Also, a user can further specify the parameters of the default query message for a series similar to the customizable query message for a study list described above.

Image Retrieval Messages

Figure 15A:
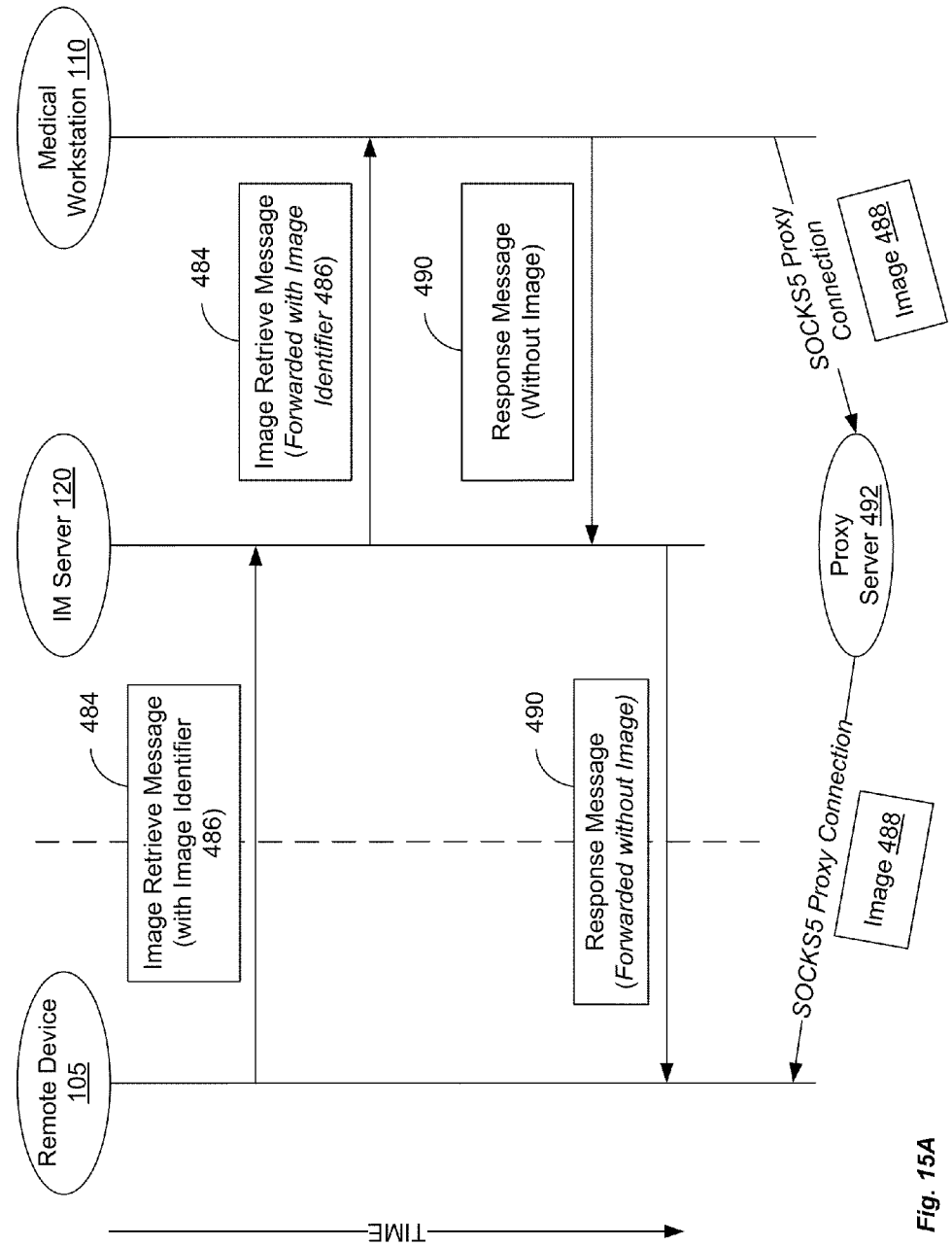
FIGS. 15A and 15C illustrate a message flow for image retrieval messages.

A user can select an image of the series list of FIG. 14B for transfer to the remote device 105 or to another medical workstation, such as the second medical workstation 135. FIG. 15A illustrates the communication flow to cause the transfer of the image associated with thumbnail 476 to the remote device 105. Upon a user selection of thumbnail 476 and receipt of user input indicating a desire to retrieve the associated image (image 488), the client IM application 145 generates an image retrieve message 484 with an identifier 486 of an image 488 associated with the thumbnail 476. The image retrieve message 484 is encrypted using the public key of the medical workstation 110 and signed using the private key of the remote device 105. The image retrieve message 484 is then sent to the IM server 120, which forwards the image retrieve message 484 to the medical workstation 110.

The API 215 and service application 210 of the medical workstation 110 verify the digital signature and decrypt the image retrieve message 484. The service application 210 verifies that the remote device 105 has permission to access the image 488 and, if so, retrieves the image 488 from the medical image database 235. The API 215 and service application 210 generate a retrieve response message 490, which is encrypted and signed and sent to the remote device 105 via the IM server 120. The retrieve response message 490 does not include the image 488. Rather, the medical workstation 110 and remote device 105 form a SOCKS5 proxy connection with a proxy server 492. The image 488 is sent from the medical workstation 110 to the remote device 105 via the SOCKS5 proxy connections and proxy server 492. In some instances, the proxy server 492 is included in the IM server 120, but still communicates according to the SOCKS5 standard.

In some instances, the image 488 is a Digital Imaging and Communications in Medicine (DICOM) image and the medical workstation 110 converts the image 488 to an image file type that requires less memory space, such as a Portable Network Graphics (PNG) file, before sending the image 488 to the remote device. In other instances, the image 488 is sent to the remote device 105 in its original format.

Figure 15B:
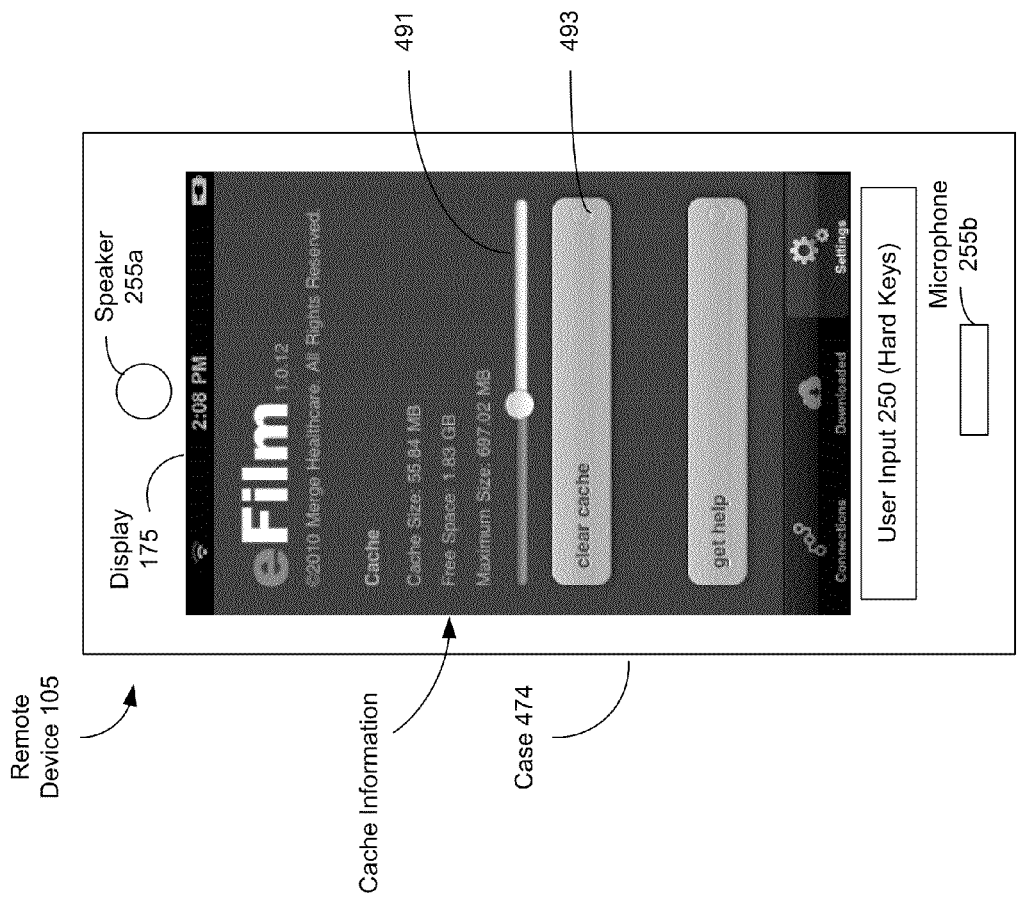
FIG. 15B illustrates a graphical user interface for software being executed on the remote device.

Upon receipt, the image 488 is stored locally on the remote device 105 within the memory 160. In some embodiments, the client IM application 145 stores images in the memory 160 in a cache-style such that, when a predetermined amount of memory space for images is exceeded, the client IM application 145 deletes the images least recently accessed. For example, FIG. 15B illustrates an exemplary GUI screen for the remote device 105 that is used to alter local memory settings. A user is able to specify the maximum amount of memory 160 space used to store images by adjusting the cache memory scroll bar 491, clear the memory 160 of stored images using the clear cache button 493, and review cache information. The cache information displayed includes the amount of memory space currently used to store images (cache size) and the total free memory space available on the remote device 105 (free space).

In some embodiments, the user is able to search, browse, view, and delete the images stored locally in the memory 160 using the client IM application 145 even when not connected to any external device, such as the IM server 120. In some instances, the client IM application 145 will still require the user to enter his or her PIN number before allowing access to stored images.

After receipt of the image 488, the image 488 is displayed on the display 175 of the remote device 105 via an image viewer of the client IM application 145. The user is able to manipulate the display of the image 488 by using the touch screen capabilities of display 175 or the user input 250. For instance, the user is able to zoom in/out, pan up/down/left/right, and reset to the original view of the image. The user is also able to select to view the image 488 text information overlaid on the image or on a text bar outside the image boundaries (e.g., below the image). In the case of a series with multiple images, the user is also able to scroll between the related images of the series.

Figure 15C:
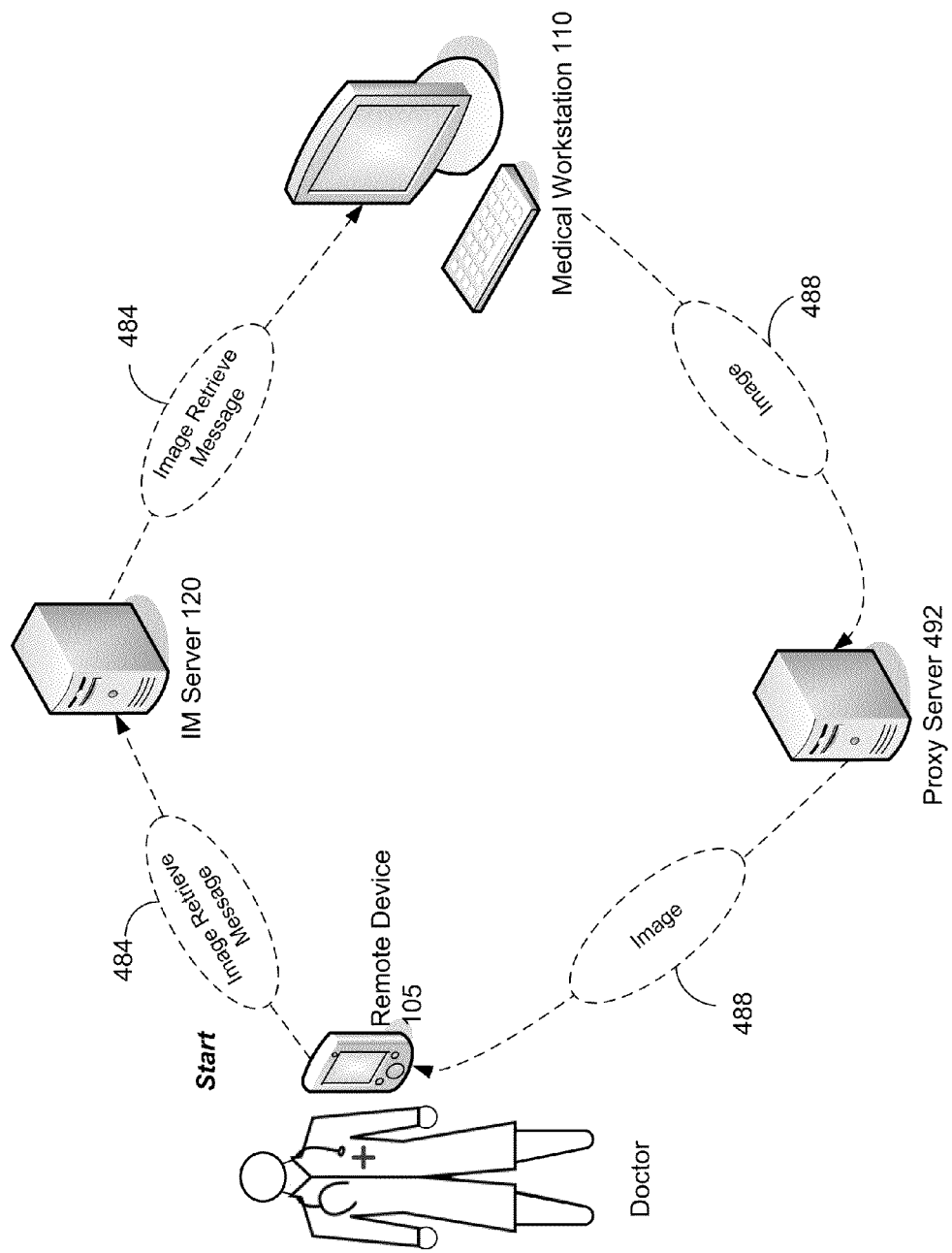

FIG. 15C provides another illustration of the communication flow of FIG. 15A, without the retrieve response message 490. Although a doctor is depicted using the remote device 105, other persons, such as medical professionals and patients, are potential users of the remote device 105.

Image Move Messages

Figure 16:
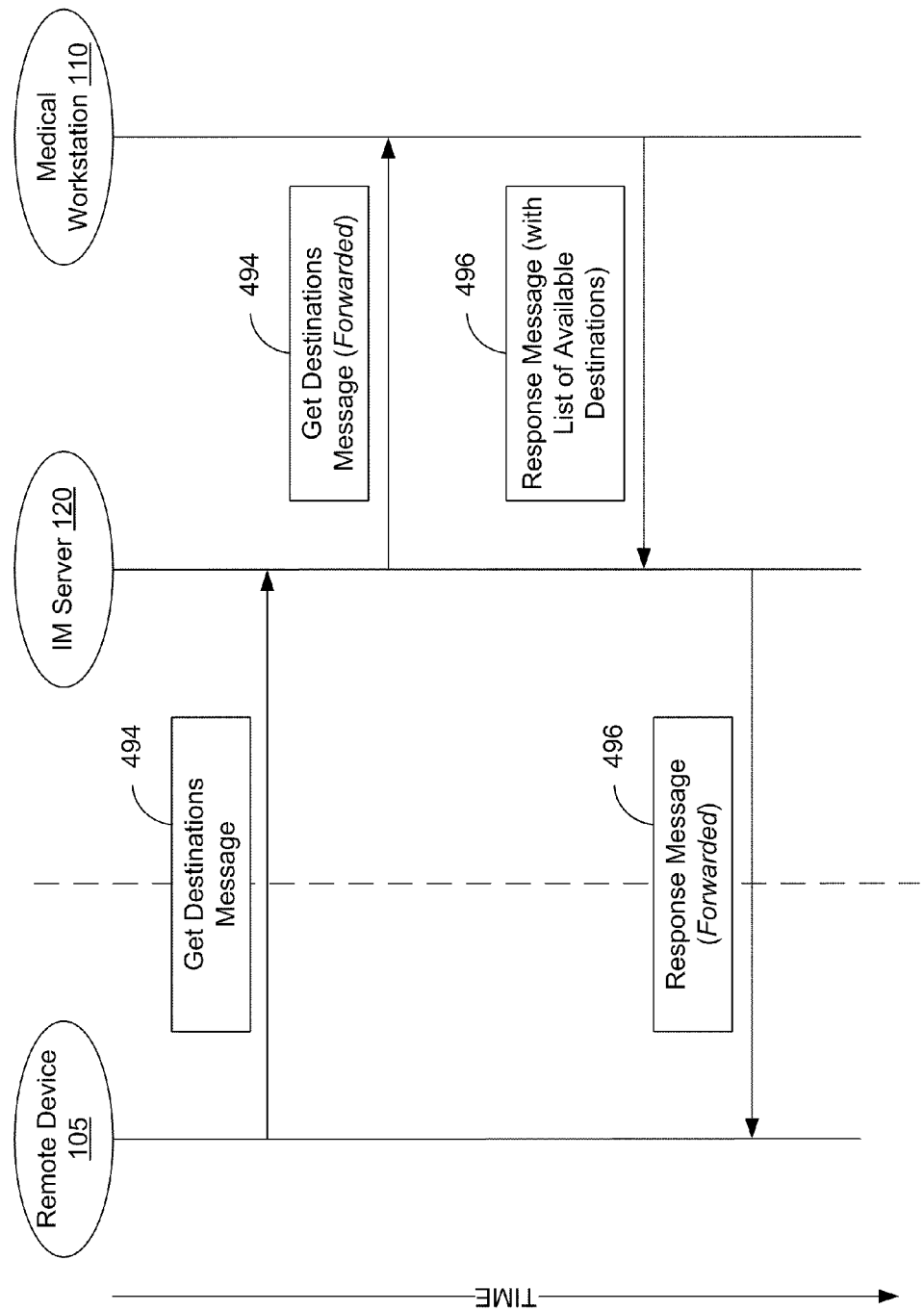
FIG. 16 illustrates a message flow for get destinations messages.

As noted above, a user can select an image of the image results list for transfer to another medical workstation, such as the second medical workstation 135. First, however, the remote device 105 is used to determine which other medical workstations are available as destinations for a selected image. FIG. 16 illustrates the communication flow between the remote device 105, medical workstation 110, and IM server 120 when a remote device 105 seeks the available destinations.

Upon receipt of user input indicating a desire to transfer an image between medical workstations, the client IM application 145 generates a get destinations message 494. The get destinations message 494 is encrypted and signed and sent to the IM server 120. The IM server 120 forwards the get destinations message 494 to the medical workstation 110.

The API 215 and service application 210 of the medical workstation 110 verify the digital signature and decrypt the get destinations message 494. The service application 210 verifies that the remote device 105 has permission to get destinations and, if so, retrieves a list of medical workstations available for image transfer. The list of medical workstations may be a generally static list or a dynamically updated list similar to a roster within rosters 290, maintained locally by the medical workstation 110 or another resource coupled to a network of the medical workstation 110. The list is stored in the memory 205 of the medical workstation 110 in some instances.

The API 215 and service application 210 generate a get destinations response message 496 including the list of medical workstation available for image transfer. The list includes an identifier for each medical workstation available, such as a nickname or a network address. The get destinations response message 496 is sent to the IM server 120, which forwards it to the remote device 105. The remote device 105 displays the list of available medical workstations, which includes the second medical workstation 135.

Figure 17A:
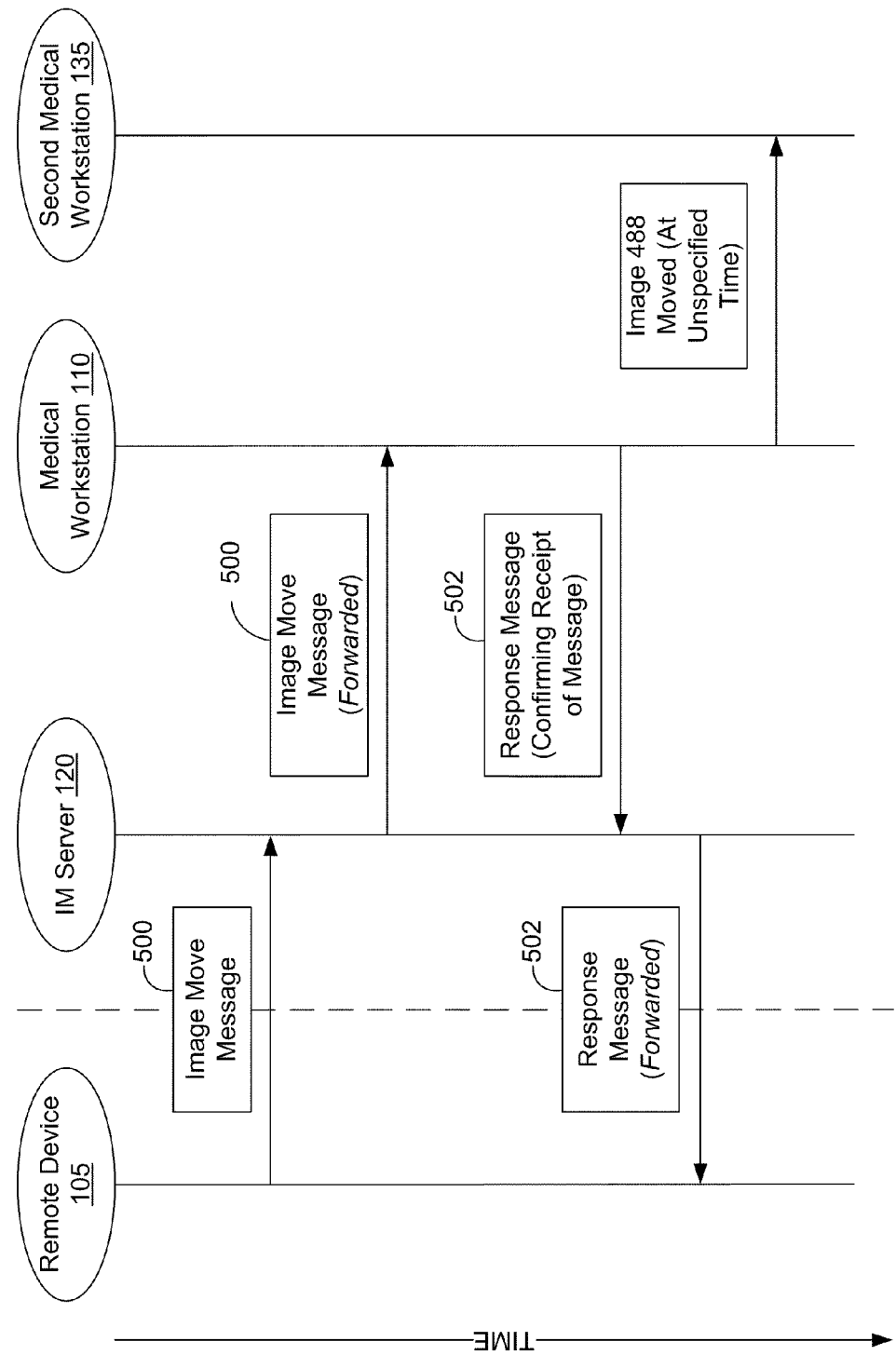

Thereafter, a user is able to select one of the available workstations to receive the image 488. FIG. 17A illustrates the communication flow between the remote device 105, medical workstation 110, IM server 120, and the second medical workstation 135 when a user of the remote device 105 selects to transfer the image 488 to the second medical workstation 135.

The client IM application 145 generates an image move message 500 specifying the second medical workstation 135 as the destination and the image 488 as the image to be moved. The image move message 500 is encrypted and signed and sent to the IM server 120. The IM server 120 forwards the image move message 500 to the medical workstation 110.

The API 215 and service application 210 of the medical workstation 110 verify the digital signature and decrypt the image move message 500. The service application 210 verifies that the remote device 105 has permission to move the image 488. If so, the API 215 and service application 210 generate a move image response message 502 acknowledging the image move message 500 and indicating the intent to move the image 488. The move image response message 502 does not indicate that the image 488 has actually been moved. The medical workstation 110 moves the image 488 to the second medical workstation 135 immediately or at some later time. The original image 488 is generally retained on the medical workstation 110, while a copy of the image 488 is sent to the second medical workstation 135. The image 488 is moved between workstations using, for instance, a LAN connection or some other suitable communication link.

FIG. 17B provides a different illustration of the communication flow of FIG. 17A, without the move image response message 502. Although a doctor is depicted using the remote device 105, other persons, such as medical professionals and patients, are potential users of the remote device 105.

Figure 17C:
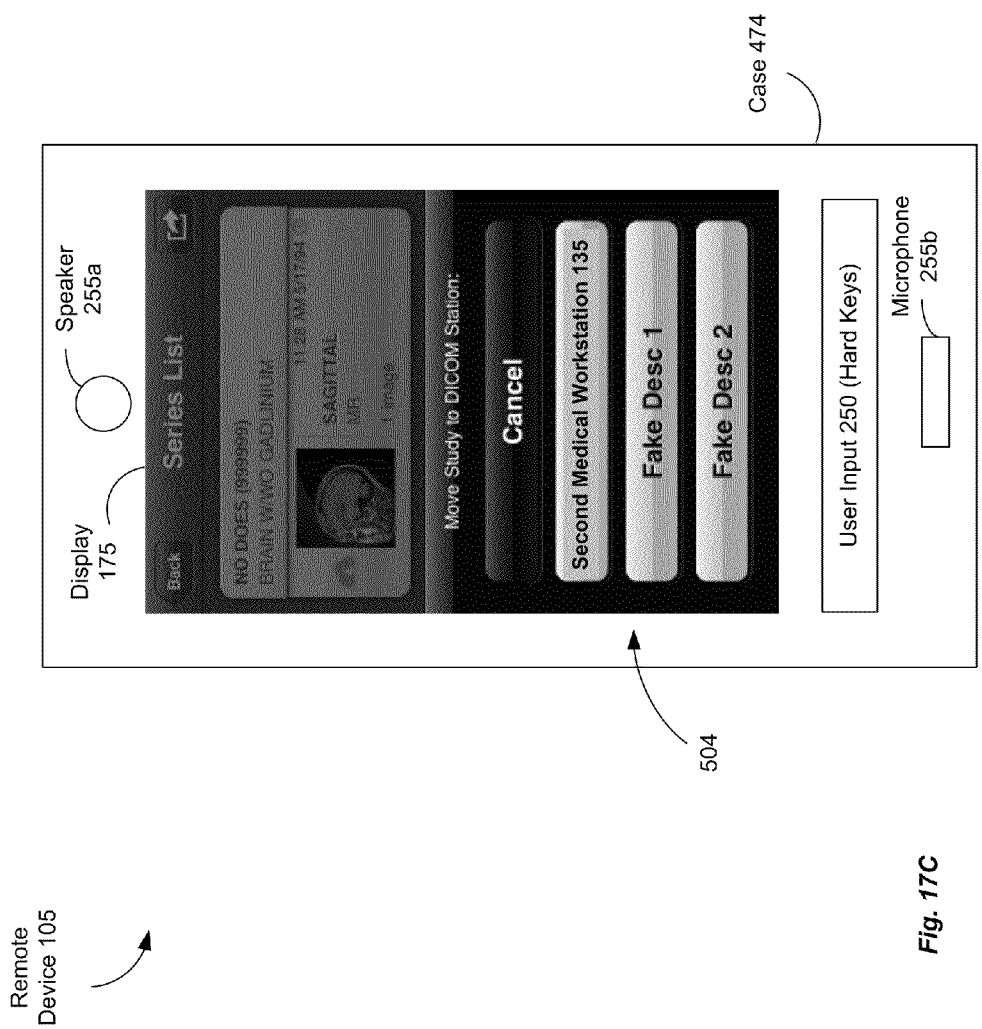
FIG. 17C illustrates a graphical user interface for software being executed on the remote device.

FIG. 17C illustrates an exemplary GUI screen for the remote device 105 that is used to select the second workstation 135 to receive an image or study on the medical workstation 110. The workstations 504 listed were retrieved from the medical workstation 110 using the get destinations message 494. Upon selection of one of the available workstations 504, the image move message 500 is generated and sent by the remote device 105 to the medical workstation 110 as described above.

Figure 18A:
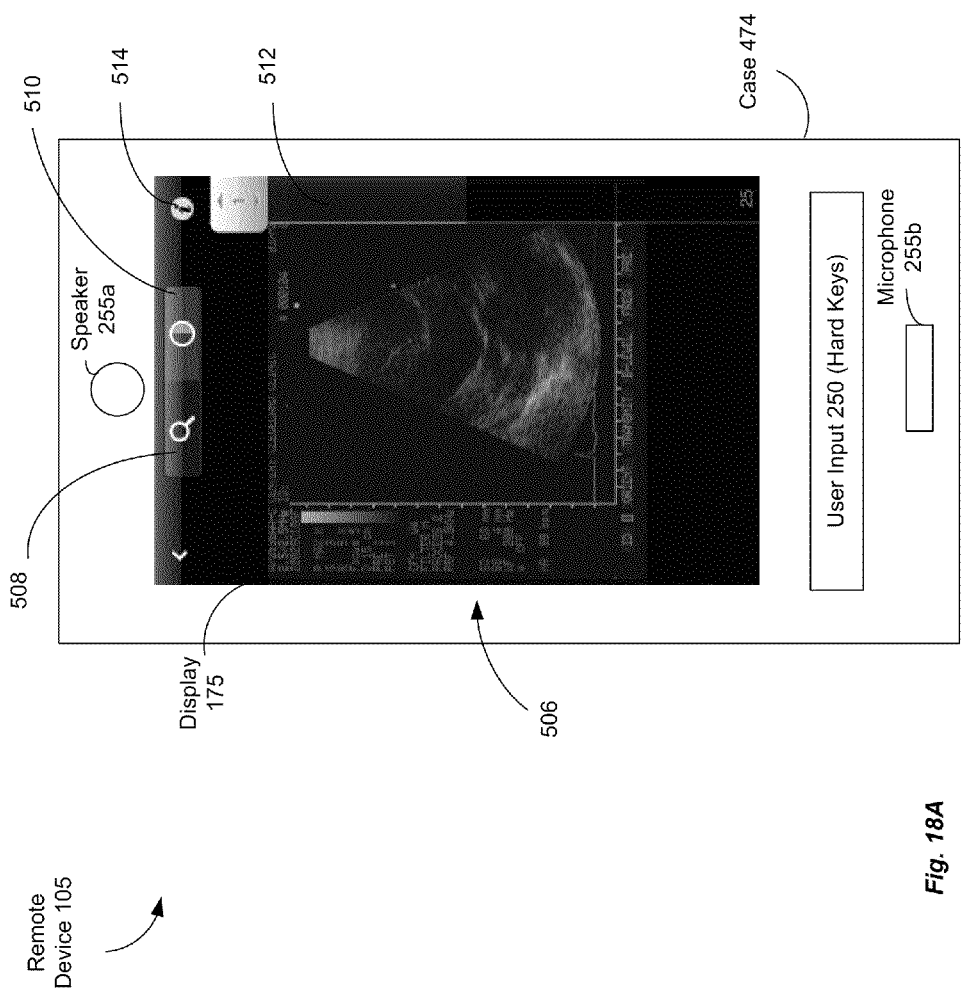
FIGS. 18A-B illustrate a graphical user interface for software being executed on the remote device.
Figure 18B:
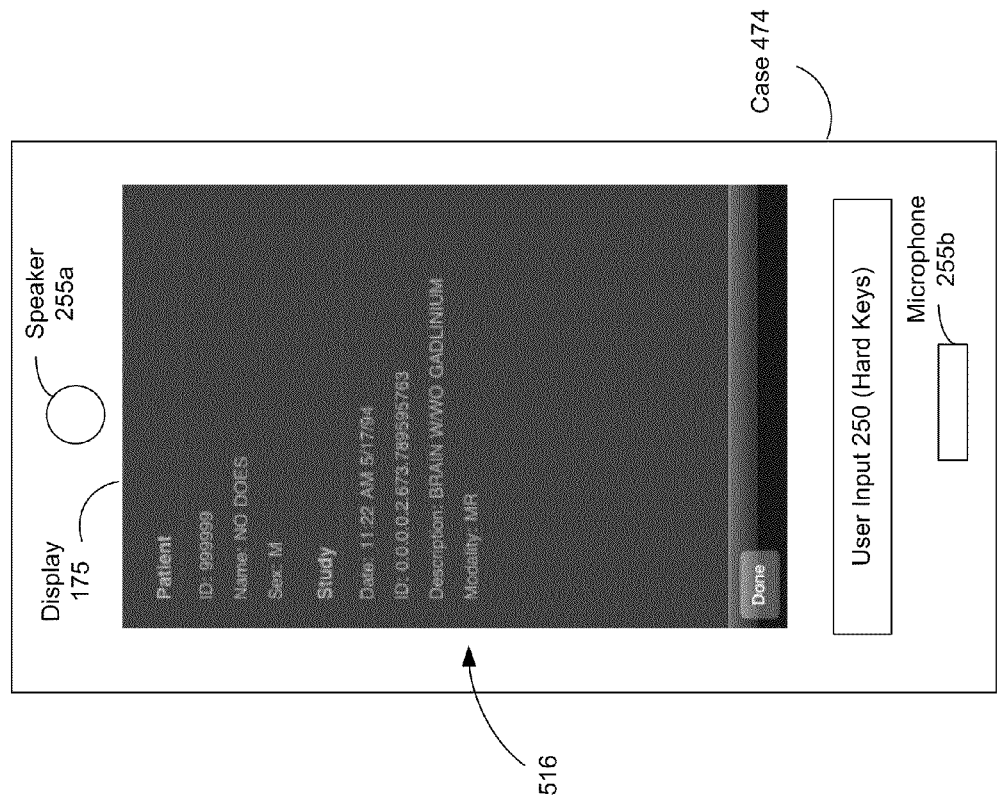

FIG. 18A illustrates an exemplary GUI screen for the remote device 105 that is used when displaying an image 506. When the image zoom/pan button 508 is enabled, a user can pan and zoom the image 506 using the touch screen display or user input 250. When the image adjust button 510 is enabled, a user can adjust the brightness and contrast using the touch screen display or user input 250. Additionally, for studies that include multiple images, a user can scroll through the images using the image scroll bar 512. In some embodiments, the image scroll bar 512 also functions as a download status indicator to indicate how much of the image 506 has been received from the medical workstation 110. The information button 514 causes the remote device 105 to display image information 516 for image 506 in an exemplary GUI screen as depicted in FIG. 18B. The image information 516 includes items such as a patient identifier number, a patient name, patient sex, date of study, study identifier number, study description, and study modality.

In some embodiments, the systems and methods described herein enable remote control of imaging workstations, remote signing of reports by radiologists, remote routing of imaging studies between locations, and/or remote access to radiology information systems and/or hospital information systems. In some embodiments, the systems and methods enable a specialist (e.g., a radiologist) or other doctor to access their system remotely. In some embodiments, the systems and methods are used by referring physicians to gain fast access to results from referred specialists and vice versa. Embodiments of the invention also enable a medical professional to send patient images to colleagues (e.g., members of a surgical team), a technologist, or other medical professionals. Additionally, embodiments of the invention provide system administrators remote access to troubleshoot a particular medical workstation 110. Furthermore, embodiments of the invention provide patients access to their own information directly from a specialist or referring physician or to send images to a particular medical professional.

Although the above embodiments are directed to image browsing, searching, transferring, etc., embodiments of the invention also include remote control of the medical workstation 110 and other devices to perform non-image related tasks. For instance, in some embodiments, the IM infrastructure is used for communicating and/or signing medical reports.

Thus, embodiments of the invention provide, among other things, systems and methods for remote control and management of medical workstations over an IM infrastructure.

What is claimed is:

1. A method of transferring medical images from a remote medical image database to a destination device using an instant messaging (IM) infrastructure comprising:
   receiving, by a user of a local device, an out-of-band communication from a remote medical workstation including a unique communication ID;
   establishing a session between the local device and an IM server;
   sending a roster update request, by the local device, to update a roster of the local device on the IM server to include the remote medical workstation, wherein the roster update request is performed if the roster update request includes the unique communication ID and is not performed if the roster update request does not include the unique communication ID;
   sending a presence message to the remote medical workstation via the IM server, wherein the remote medical workstation communicates with a medical image database and includes a user interface with a display enabling a user of the remote medical workstation to select one or more images from the medical image database to be viewed on the display;
   receiving, by the local device, presence information for the remote medical workstation from the IM server;
   sending, by the local device, an image availability query message to the remote medical workstation via the IM server;
   obtaining, by the local device, image availability data from the remote medical workstation via the IM server, wherein the image availability data indicates an image that is available on the remote medical image database;
   displaying, on the local device, a representation of the image available on the remote medical image database;
   receiving, at the local device, a user selection of the image; and
   sending an image command message, based on the user selection, to the remote medical workstation via the IM server, wherein the image command message instructs the remote medical workstation to transmit a copy of the image to the destination device.

2. The method of claim 1, wherein the destination device is a second remote medical workstation.

3. The method of claim 2, further comprising
   sending a get destinations message to the remote medical workstation via the IM server, and
   receiving a get destinations response message from the remote medical workstation via the IM server, wherein the get destinations response message indicates that the second remote medical workstation is available to receive a file transfer from the remote medical workstation.

4. The method of claim 1, wherein the destination device is the local device and the local device receives the copy of the image.

5. The method of claim 4, wherein the local device receives the copy of the image via a proxy server.

6. The method of claim 1, wherein the copy of the image is generated by converting the image from a first file type with a first file size to a second file type with a second, smaller file size.

7. The method of claim 6, wherein the first file type is a Digital Imaging and Communications in Medicine (DICOM) image type.

8. The method of claim 1, wherein at least one of the image availability query message and the image command message is encrypted using a public key.

9. The method of claim 1, wherein the user selection of the image is made by way of a graphical user interface displayed on the local device and the image command message is not shown on a display of the local device.

10. The method of claim 1,
wherein the unique communication ID is generated by a client device of the IM server other than the local device and the remote medical workstation; and
wherein the roster update request further includes a nickname identifying the remote medical workstation.

11. The method of claim 1, wherein the local device is a mobile phone.

12. A method of transmitting medical images from a medical image database to a remote device using an instant messaging (IM) infrastructure comprising:
establishing a first session between an IM server and the remote device;
establishing a second session between the IM server and a medical workstation, wherein the medical workstation communicates with the medical image database,
includes a user interface with a display enabling a user of the medical workstation to select one or more images from the medical database to be viewed on the display, and
requests and receives a unique communication ID and provides the unique communication ID to a user of the remote device in an out-of-band communication;
receiving a roster update request, for the remote device, to update a roster of the remote device on the IM server to include the medical workstation, wherein the roster update request is performed if the roster update request includes the unique communication ID and is not performed if the roster update request does not include the unique communication ID;
sending, by the IM server, roster and presence information to the remote device based on a roster request message received from the remote device;
forwarding, by the IM server, an image availability query message from the remote device to the medical workstation;
forwarding, by the IM server, image availability data received from the medical workstation to the remote device, wherein the image availability data includes a representation of an image available on the medical image database; and
forwarding, by the IM server, an image command message with an image selection received from the remote device to the medical workstation, wherein the image command message instructs the medical workstation to transfer a copy of the selected image to a destination device.

13. The method of claim 12, wherein the destination device is a second medical workstation.

14. The method of claim 13, further comprising
forwarding a get destinations message from the remote device to the medical workstation, and
forwarding a get destinations response message from the medical workstation to the remote device, wherein the get destinations response message indicates that the second medical workstation is available to receive a file transfer from the medical workstation.

15. The method of claim 12, wherein the destination device is the remote device.

16. The method of claim 12, further comprising
receiving, from a web server, a request to create an account and a roster for the remote device; and
creating the account and the roster for the remote device, wherein the roster is created to include a client device other than the medical workstation.

17. A method of transmitting medical images from a medical image database to a remote device using an instant messaging (IM) infrastructure comprising:
receiving a local image selection on a user interface of a medical workstation from a user of the medical workstation;
displaying the locally selected image on a display of the medical workstation;
receiving, by the medical workstation, a nickname of the remote device entered by the user at the medical workstation;
requesting, by the medical workstation, a unique communication ID associated with the nickname and the remote device;
providing, to a user of the remote device, an out-of-band communication from a medical workstation including the unique communication ID;
establishing, by the medical workstation, a session with an IM server;
receiving, by the medical workstation in communication with the medical image database, presence information for the remote device from the IM server;
receiving, by the medical workstation, an image availability query message from the remote device via the IM server;
transmitting, by the medical workstation, image availability data to the remote device via the IM server, wherein the image availability data includes a representation of an image available on the medical image database;
receiving an image command message with an image selection from the remote device via the IM server, wherein the image selection selects for transmission the image available on the medical image database; and
transmitting a copy of the image to a destination device in response to the image command message.

18. The method of claim 17, wherein the destination device is a second medical workstation and the medical workstation sends the copy of the image to the second medical workstation.

19. The method of claim 18, further comprising
receiving, by the medical workstation, a get destinations message from the remote device via the IM server, and
sending, by the medical workstation, a get destinations response message from to the remote device via the IM server, wherein the get destinations response message indicates that the second medical workstation is available to receive a file transfer from the medical workstation.

20. The method of claim 17, wherein the destination device is the remote device and the medical workstation sends the copy of the image to the remote device via a proxy server.

21. The method of claim 20, wherein the copy of the image is generated by converting the image from a first file type with a first file size to second file type with a second, smaller file size.

22. The method of claim 17, wherein at least one of the image availability query message and the image command message is encrypted using a public key of the remote device and is decrypted using a private key of the medical workstation.

23. An instant messaging (IM) server enabling instant message communication between a medical workstation and a requesting device, the medical workstation in communication with a medical database, the IM server comprising
 a memory including
  i. a requesting device roster including an identification for the medical workstation,
  ii. a medical workstation roster including an identification for the requesting device, and
  iii. presence information indicating presence status of the requesting device and the medical workstation;
 a roster management module that updates the requesting device roster to include the medical workstation dependent on a roster update request sent from the requesting device including a nickname of the medical workstation and a unique communication ID, wherein the unique communication ID is provided in an out-of-band communication from the medical workstation;
 a session establishing module that
  i. establishes a first instant message session between the IM server and the requesting device, and
  ii. establishes a second instant message session between the IM server and the medical workstation; and
 a message routing module that
  i. forwards an image availability query message from the requesting device to the medical workstation,
  ii. forwards image availability data received from the medical workstation to the requesting device, wherein the image availability data includes a representation of an image available on the medical image database,
  iii. forwards an image command message with an image selection from the requesting device to the medical workstation, wherein the image command message instructs the medical workstation to transfer a copy of the selected image to a destination device.

24. The IM server of claim 23 further comprising a presence module that
 updates the presence information based on received presence messages from the requesting device and the medical workstation, and
 transmits the presence information based on presence queries from the requesting device and the medical workstation.

25. A method of establishing a secure instant message (IM) session between a local device and a remote medical workstation comprising:
 a. creating an IM account for the local device on an IM server by submitting registration information to a registration server, wherein the registration server communicates with the IM server to
  i. create an IM account identifier using the registration information,
  ii. add the IM account identifier to a first roster associated with a registration BOT maintained by the IM server, and
  iii. add a BOT identifier to a second roster associated with the IM account identifier;
 b. receiving, by the local device, a temporary unique ID from the remote medical workstation, wherein the temporary unique ID is provided to the remote medical workstation by the registration BOT;
 c. requesting, by the local device, that the registration BOT add the remote medical workstation to the second roster and add the local device to a third roster associated with the remote medical workstation, wherein the request is denied unless the temporary unique ID is provided to the registration BOT; and
 d. sending, by the local device, a message via the IM server to the remote medical workstation that requests transmission of an image on the remote medical workstation to a destination device.

26. The method of claim 25, wherein the registration information includes a personal identification number (PIN), an email address, and a password.

27. The method of claim 25, wherein the destination device is the local device and the local device receives the image.

28. The method of claim 25, wherein the destination device is a second remote medical workstation.

29. The method of claim 25, further comprising
 a. generating a public/private key pair including a public key and a private key;
 b. storing the private key on the local device; and
 c. providing the public key to the IM server.

30. A client instant messaging (IM) application stored on a computer readable medium that, when executed by a processor of a local device, is operable to
 receive, by a user of a local device, an out-of-band communication from a remote medical workstation including a unique communication ID;
 establish a session between the local device and an IM server;
 send a roster update request, by the local device, to update a roster of the local device on the IM server to include the remote medical workstation, wherein the roster update request is performed if the roster update request includes the unique communication ID and is not performed if the roster update request does not include the unique communication ID;
 send a presence message to the remote medical workstation via the IM server, wherein the remote medical workstation communicates with a medical image database and includes a user interface with a display enabling a user of the remote medical workstation to select one or more images from the medical image database to be viewed on the display;
 receive presence information for the remote medical workstation from the IM server;
 send an image availability query message to the remote medical workstation via the IM server;
 obtain image availability data from the remote medical workstation via the IM server, wherein the image availability data indicates an image that is available on a remote medical image database;
 display, on a display screen of the local device, a representation of the image available on the remote medical image database;
 receive a user selection of the image; and
 send an image command message, based on the user selection, to the remote medical workstation via the IM server, wherein the image command message instructs the remote medical workstation to transmit a copy of the image to a destination device.

31. A medical workstation that is remotely controllable by a remote device via an instant messaging (IM) server, the medical workstation including a processor and a service application, which, when executed by the processor, is operable to
- receive a local image selection on a user interface of the medical workstation from a user of the medical workstation;
- display the locally selected image on a display of the medical workstation;
- receive, by the medical workstation, a nickname of the remote device entered by the user at the medical workstation;
- request, by the medical workstation, a unique communication ID associated with the nickname and the remote device;
- provide, to a user of the remote device, an out-of-band communication from a medical workstation including the unique communication ID;
- establish a session with the IM server;
- receive presence information for the remote device from the IM server;
- receive an image availability query message from the remote device via the IM server;
- transmit image availability data to the remote device via the IM server, wherein the image availability data includes a representation of an image available on the medical image database;
- receive an image command message with an image selection from the remote device via the IM server, wherein the image selection selects for transmission the image available on the medical image database; and
- transmit a copy of the image to a destination device in response to the image command message.

* * * * *